(12) United States Patent
Rudie et al.

(10) Patent No.: US 10,179,029 B2
(45) Date of Patent: Jan. 15, 2019

(54) COOLED MICROWAVE DENERVATION CATHETER CONFIGURATION AND METHOD

(71) Applicant: Denervx LLC, Maple Grove, MN (US)

(72) Inventors: Eric N. Rudie, Maple Grove, MN (US); Philip J. Haarstad, Chanhassen, MN (US); Stanley E. Kluge, Watertown, MN (US)

(73) Assignee: Denervx LLC, Maple Grove, MN (US)

( * ) Notice: Subject to any disclaimer, the term of this patent is extended or adjusted under 35 U.S.C. 154(b) by 0 days.

(21) Appl. No.: 15/881,083

(22) Filed: Jan. 26, 2018

(65) Prior Publication Data

US 2018/0147010 A1    May 31, 2018

Related U.S. Application Data

(62) Division of application No. 14/605,556, filed on Jan. 26, 2015.
(Continued)

(51) Int. Cl.
*A61B 18/18* (2006.01)
*A61B 18/00* (2006.01)

(52) U.S. Cl.
CPC ... *A61B 18/1815* (2013.01); *A61B 2018/00023* (2013.01); *A61B 2018/00029* (2013.01);
(Continued)

(58) Field of Classification Search
CPC . A61B 18/1492; A61B 18/18; A61B 18/1815; A61B 2018/183;
(Continued)

(56) References Cited

U.S. PATENT DOCUMENTS

| | | | |
|---|---|---|---|
| 5,304,214 A | | 4/1994 | DeFord et al. |
| 5,496,271 A | * | 3/1996 | Burton .................. A61B 18/18 |
| | | | 604/101.05 |

(Continued)

OTHER PUBLICATIONS

Waleska, C., "Animal models for the study of arterial hypertension", Journal of Biosciences, vol. 36, No. 4, Sep. 2011, 7 pages.
(Continued)

*Primary Examiner* — Eunhwa Kim
(74) *Attorney, Agent, or Firm* — Kinney & Lange, P.A.

(57) ABSTRACT

A method of performing denervation with a cooled microwave denervation catheter assembly includes advancing a catheter body over a guide wire in a body lumen of a patient to a treatment location adjacent targeted nerves, with the guide wire being located in an interior lumen of the catheter body, inflating the balloon with cooling fluid to contact a wall of the body lumen of the patient, removing the guide wire from the interior lumen of the catheter body, and inserting a microwave antenna catheter into the interior lumen of the catheter body, so that denervation treatment may be performed by simultaneously circulating cooling fluid in the balloon and supplying power to the microwave antenna, to cause the targeted nerves to be heated to a temperature sufficient to cause thermal damage while the wall of the body lumen is maintained at a temperature where thermal damage does not occur.

3 Claims, 24 Drawing Sheets

Related U.S. Application Data

(60) Provisional application No. 61/931,420, filed on Jan. 24, 2014.

(52) U.S. Cl.
CPC ............ A61B 2018/00285 (2013.01); A61B 2018/1846 (2013.01)

(58) Field of Classification Search
CPC .... A61B 2018/1861; A61B 2018/0022; A61B 2018/00285; A61B 2018/1838; A61B 2018/1853; A61B 2018/00404; A61B 2018/00398; A61B 2018/00511
See application file for complete search history.

(56) References Cited

U.S. PATENT DOCUMENTS

| | | | |
|---|---|---|---|
| 5,620,480 A | 4/1997 | Rudie | |
| 5,649,973 A | 7/1997 | Tierney et al. | |
| 5,979,454 A | 11/1999 | Knvari et al. | |
| 5,987,360 A | 11/1999 | McGrath et al. | |
| 6,047,216 A | 4/2000 | Carl et al. | |
| 6,106,518 A | 8/2000 | Wittenberger et al. | |
| 6,122,551 A | 9/2000 | Rudie et al. | |
| 6,223,085 B1* | 4/2001 | Dann | A61B 18/1492 606/29 |
| 6,272,384 B1 | 8/2001 | Simon et al. | |
| 6,283,959 B1 | 9/2001 | Lalonde et al. | |
| 6,283,988 B1 | 9/2001 | Laufer et al. | |
| 6,289,249 B1 | 9/2001 | Arndt et al. | |
| 6,427,089 B1 | 7/2002 | Knowlton | |
| 6,490,488 B1 | 12/2002 | Rudie et al. | |
| 6,512,956 B2 | 1/2003 | Arndt et al. | |
| 6,514,249 B1 | 2/2003 | Maguire et al. | |
| 6,592,579 B2 | 7/2003 | Arndt et al. | |
| 6,740,108 B1 | 5/2004 | Just et al. | |
| 6,807,446 B2 | 10/2004 | Fenn et al. | |
| 6,918,869 B2 | 7/2005 | Shaw et al. | |
| 7,052,508 B2 | 5/2006 | Werneth | |
| 7,081,112 B2 | 7/2006 | Joye et al. | |
| 7,097,641 B1 | 8/2006 | Arless et al. | |
| 7,132,439 B2 | 11/2006 | Wang et al. | |
| 7,162,303 B2 | 1/2007 | Levin et al. | |
| 7,226,446 B1* | 6/2007 | Mody | A61B 18/18 606/33 |
| 7,311,703 B2 | 12/2007 | Turovskiy et al. | |
| 7,465,300 B2 | 12/2008 | Arless et al. | |
| 7,617,005 B2 | 11/2009 | Demarais et al. | |
| 7,620,451 B2 | 11/2009 | Demarais et al. | |
| 7,647,115 B2 | 1/2010 | Levin et al. | |
| 7,717,948 B2 | 5/2010 | Demarais et al. | |
| 7,756,583 B2 | 7/2010 | Demarais et al. | |
| 7,840,271 B2 | 11/2010 | Kieval et al. | |
| 7,853,333 B2 | 12/2010 | Demarais | |
| 7,875,024 B2 | 1/2011 | Turovskiy et al. | |
| 7,925,352 B2 | 4/2011 | Stack et al. | |
| 7,937,143 B2 | 5/2011 | Demarais et al. | |
| 7,951,140 B2 | 5/2011 | Arless et al. | |
| 8,083,732 B2 | 12/2011 | Arless et al. | |
| 8,131,371 B2 | 3/2012 | Demarais et al. | |
| 8,131,372 B2 | 3/2012 | Levin et al. | |
| 8,140,170 B2 | 3/2012 | Rezai et al. | |
| 8,287,526 B2 | 10/2012 | Arless et al. | |
| 8,473,069 B2 | 6/2013 | Bi et al. | |
| 8,548,600 B2 | 10/2013 | Deem et al. | |
| 8,568,399 B2 | 10/2013 | Azamian et al. | |
| 8,620,423 B2 | 12/2013 | Demarais et al. | |
| 8,626,300 B2 | 1/2014 | Demarais et al. | |
| 8,641,709 B2 | 2/2014 | Sauvageau et al. | |
| 8,652,129 B2 | 2/2014 | Wu et al. | |
| 8,676,309 B2 | 3/2014 | Deem et al. | |
| 8,740,985 B1 | 6/2014 | Mayse et al. | |
| 8,777,943 B2 | 7/2014 | Mayse et al. | |
| 8,808,280 B2 | 8/2014 | Mayse et al. | |
| 8,821,489 B2 | 9/2014 | Mayse et al. | |
| 2003/0055471 A1 | 3/2003 | Fenn et al. | |
| 2003/0163118 A1 | 8/2003 | Hamilton et al. | |
| 2005/0249667 A1 | 11/2005 | Tuszynski et al. | |
| 2005/0288730 A1 | 12/2005 | Deem et al. | |
| 2006/0041277 A1 | 2/2006 | Deem et al. | |
| 2006/0111704 A1 | 5/2006 | Brenneman et al. | |
| 2007/0129720 A1 | 6/2007 | Demarais et al. | |
| 2007/0142879 A1 | 6/2007 | Greenberg et al. | |
| 2007/0203551 A1 | 8/2007 | Cronin et al. | |
| 2008/0221650 A1* | 9/2008 | Turner | A61B 18/1206 607/102 |
| 2008/0255642 A1 | 10/2008 | Zarins et al. | |
| 2008/0294155 A1 | 11/2008 | Cronin | |
| 2009/0024195 A1 | 1/2009 | Rezai et al. | |
| 2009/0062873 A1 | 3/2009 | Wu et al. | |
| 2009/0076409 A1 | 3/2009 | Wu et al. | |
| 2009/0270838 A1* | 10/2009 | Berthiaume | A61F 2/95 604/524 |
| 2010/0125269 A1* | 5/2010 | Emmons | A61B 18/1815 606/33 |
| 2010/0137860 A1 | 6/2010 | Demarais et al. | |
| 2010/0168731 A1 | 7/2010 | Wu et al. | |
| 2010/0174282 A1 | 7/2010 | Demarais et al. | |
| 2010/0222851 A1 | 9/2010 | Deem et al. | |
| 2010/0262137 A1* | 10/2010 | Nye | A61B 18/18 606/33 |
| 2011/0060324 A1 | 3/2011 | Wu et al. | |
| 2011/0092781 A1 | 4/2011 | Gertner | |
| 2011/0184337 A1 | 7/2011 | Evans et al. | |
| 2011/0200171 A1 | 8/2011 | Beetel et al. | |
| 2011/0257523 A1 | 10/2011 | Hastings et al. | |
| 2011/0257562 A1 | 10/2011 | Schaer | |
| 2011/0257564 A1 | 10/2011 | Demarais et al. | |
| 2011/0264075 A1 | 10/2011 | Leung et al. | |
| 2011/0264086 A1 | 10/2011 | Ingle | |
| 2011/0264116 A1 | 10/2011 | Kocur et al. | |
| 2011/0306904 A1 | 12/2011 | Jacobson et al. | |
| 2011/0307034 A1 | 12/2011 | Hastings et al. | |
| 2012/0019079 A1 | 1/2012 | Ziegler et al. | |
| 2012/0029495 A1 | 2/2012 | Wittenberger | |
| 2012/0029496 A1 | 2/2012 | Smith | |
| 2012/0029510 A1 | 2/2012 | Haverkost | |
| 2012/0029512 A1 | 2/2012 | Willard et al. | |
| 2012/0029513 A1 | 2/2012 | Smith et al. | |
| 2012/0059286 A1 | 3/2012 | Hastings et al. | |
| 2012/0065506 A1 | 3/2012 | Smith | |
| 2012/0089047 A1 | 4/2012 | Ryba et al. | |
| 2012/0101413 A1 | 4/2012 | Beetel et al. | |
| 2012/0116383 A1 | 5/2012 | Mauch et al. | |
| 2012/0116486 A1 | 5/2012 | Naga et al. | |
| 2012/0123243 A1 | 5/2012 | Hastings | |
| 2012/0130359 A1 | 5/2012 | Turovskiy | |
| 2012/0130458 A1 | 5/2012 | Ryba et al. | |
| 2012/0136350 A1 | 5/2012 | Goshgarian et al. | |
| 2012/0143097 A1 | 6/2012 | Pike, Jr. | |
| 2012/0172863 A1 | 7/2012 | Brannan | |
| 2012/0191079 A1 | 7/2012 | Moll et al. | |
| 2012/0191083 A1 | 7/2012 | Moll et al. | |
| 2012/0232436 A1 | 9/2012 | Warnking | |
| 2012/0259269 A1 | 10/2012 | Meyer | |
| 2012/0259326 A1 | 10/2012 | Brannan et al. | |
| 2012/0265198 A1 | 10/2012 | Crow et al. | |
| 2012/0296329 A1 | 11/2012 | Ng | |
| 2012/0330306 A1 | 12/2012 | Long et al. | |
| 2013/0053732 A1 | 2/2013 | Heuser | |
| 2013/0079835 A1 | 3/2013 | Sluijter et al. | |
| 2013/0085493 A1 | 4/2013 | Bloom et al. | |
| 2013/0090647 A1 | 4/2013 | Smith | |
| 2013/0090650 A1 | 4/2013 | Jenson et al. | |
| 2013/0090652 A1 | 4/2013 | Jenson | |
| 2013/0116683 A1 | 5/2013 | Shadduck et al. | |
| 2013/0116687 A1 | 5/2013 | Willard | |
| 2013/0131668 A1 | 5/2013 | Scheer | |
| 2013/0144251 A1 | 6/2013 | Sobotka | |
| 2013/0144283 A1 | 6/2013 | Barman | |
| 2013/0158441 A1 | 6/2013 | Demarais et al. | |
| 2013/0158442 A1 | 6/2013 | Demarais et al. | |
| 2013/0165822 A1 | 6/2013 | Demarais et al. | |

(56) References Cited

U.S. PATENT DOCUMENTS

| | | |
|---|---|---|
| 2013/0165917 A1 | 6/2013 | Mathur et al. |
| 2013/0165923 A1 | 6/2013 | Mathur et al. |
| 2013/0165925 A1 | 6/2013 | Mathur et al. |
| 2013/0165926 A1 | 6/2013 | Mathur et al. |
| 2013/0172877 A1 | 7/2013 | Subramaniam et al. |
| 2013/0172881 A1 | 7/2013 | Hill et al. |
| 2013/0178824 A1 | 7/2013 | Buelna |
| 2013/0197555 A1 | 8/2013 | Scheer |
| 2013/0204241 A1 | 8/2013 | Baust |
| 2013/0274658 A1 | 10/2013 | Steinke et al. |
| 2013/0274731 A1 | 10/2013 | Anderson et al. |
| 2013/0274735 A1 | 10/2013 | Hastings et al. |
| 2013/0289369 A1 | 10/2013 | Margolis |
| 2013/0289678 A1 | 10/2013 | Clark et al. |
| 2013/0296767 A1 | 11/2013 | Zarins et al. |
| 2013/0296853 A1 | 11/2013 | Sugimoto et al. |
| 2013/0304047 A1 | 11/2013 | Grunewald et al. |
| 2013/0304052 A1 | 11/2013 | Rizq et al. |
| 2014/0012251 A1 | 1/2014 | Himmelstein et al. |
| 2014/0018605 A1 | 1/2014 | Soltesz et al. |
| 2014/0018794 A1 | 1/2014 | Anderson et al. |
| 2014/0025069 A1 | 1/2014 | Willard et al. |
| 2014/0039487 A1 | 2/2014 | Brannan et al. |
| 2014/0042154 A1 | 2/2014 | Cronin et al. |
| 2014/0046175 A1 | 2/2014 | Ladtkow et al. |
| 2014/0046313 A1 | 2/2014 | Pederson et al. |
| 2014/0046316 A1 | 2/2014 | Ladtkow et al. |
| 2014/0066915 A1 | 3/2014 | Zhou et al. |
| 2014/0066916 A1 | 3/2014 | Coe et al. |
| 2014/0066920 A1 | 3/2014 | Azamian et al. |
| 2014/0066921 A1 | 3/2014 | Coe et al. |
| 2014/0066922 A1 | 3/2014 | Coe et al. |
| 2014/0081259 A1 | 3/2014 | Deem et al. |
| 2014/0107639 A1 | 4/2014 | Zhang et al. |
| 2014/0114215 A1 | 4/2014 | Melder et al. |
| 2014/0114305 A1 | 4/2014 | Zarins et al. |

OTHER PUBLICATIONS

White, C. "Figure 7. A 0.035-in J-wire is advance beyond the tip of the guide catheter during initial cannulation (A)", America Heart Association—Journal of Circulation: Cardiovascular Intervention, vol. 3, 2010, 2 pages.

White, Christopher J., "Optimizing Outcomes for Renal Artery Intervention", American Heart Association—Journal of Circulation: Cardiovascular Intervention, vol. 3, 2010, 10 pages.

Witkowski, Adam, "Catheter-based renal sympathetic denervation for the treatment of resistant hypertension in Poland—experts consensus statement", Kardiologia Polska, vol. 69, No. 11, 2011, 4 pages.

Xu, D., "Experimental nerve thermal injury", Department of Medicine, University of Otago, Dunedin, New Zealand, vol. 117, Apr. 1994, 2 pages.

Yamamoto, T., "Figure Illustrating Horizontal Plane of Aorta & Renal Artery Intersection", American Heart Associat: Arteriosclerosis, Thrombosis, and Vascular Biology, vol. 16, 1996, 1 page.

Zanchetti, Alberto, "Carotid Baroreflex Physiology and Baroreflex Activation Therapy Mechanism of Action", Centro di Fisiologia Clinica e Ipertensione, Universita di Milano, Aug. 30, 2012, 19 pages.

Zeller, Prof. Dr. T., "Renal Denervation Therapy: Tips & Tricks", Herz-Zentrum Bad Krozingen, Germany, May 14, 2012, 35 pages.

Atherton, Daniel S., "Micro-anatomy of the renal sympathetic nervous system: A human postmortem histologic study", Clinical Anatomy, published: Oct. 4, 2011, 10 pages.

Bakris, G.L., "Baroreflex Activation Therapy provides durable benefit in patients with resistant hypertension: results of long-term follow-up in the Rheos Pivotal Trial", Journal of American Society of Hypertension, published: Mar. 6, 2012, 1 page.

Banerjee, Subhash, "Transcatheter Renal Denervation", Journal of Invasive Cardiology, created Mar. 5, 2012, 3 pages.

Bederson, J.B., "Evaluation of 2,3,5-triphenyltetrazolium chloride as a stain for detection and quantification of experimental cerebral infarction in rats", Journal of the American Heart Association, vol. 17, No. 6, 1986, 6 pages.

Bergman, Ronald A., "Opus II: Cardiovascular System: Arteries: Abdomen: Renal Arteries", Anatomy Atlases: Illustrated Encyclopedia of Human Anatomic Variation, accessed: Mar. 26, 2012, 6 pages.

Bisognano, J.D., "Baroreflex activation therapy lowers blood pressure in patients with resistant hypertension: results from the double-blind, randomized, placebo-controlled rheos pviotal trial", Journal of American College of Cardiology, Jan. 31, 2012, 2 pages.

Bobrie, Guillaume, "Device-Based Antihypertensive Therapy: Therapeutic Modulation of the Autonomic Nervous System", Hospital European Georges-Pompidou, Paris, France, created Nov. 16, 2012, 56 pages.

Braunwald, Eugene, "Introduction to Symposium", Aug. 30, 2011, 11 pages.

Cerny, Joseph C., "Aberrant Renal Arteries", Department of Surgery, Section of Urology, University of Michigan Medical Center and Henry Ford Hospital, Urology, vol. II, No. 6, Dec. 1973, 4 pages.

"Dielectric Constant of some common Liquids: Common fluids and their dielectric constant or permittivity", The Engineering ToolBox, accessed Jun. 14, 2012, https://www.engineeringtoolbox.com/liquid-dielectric-constants-d_1263.html, 3 pages.

Gabriel, Dr. Camelia, "Compilation of the Dielectric Properties of Body Tissues at RF and Microwave Frequencies", Department of Physics—King's College London, Dec. 14, 1995, 7 pages.

Hartman, Jake, "Renal Denervation: The Next Big Thing in Treating Hypertension", The Advisory Board Company, Oct. 11, 2011, 1 page.

Hasenfuss, Gerd, "New Generation Barostim neo(TM) System: Preliminary Results and Discussion", Heart Center and Heart Research Center—University of Goettingen, Germany. Created Nov. 16, 2012, 19 pages.

Jaff, Michael R., "Renal Artery Stenting is Still Alive and Well!" Massachusetts General Hospital: Vascular Center, Dec. 5, 2011, 29 pages.

Jeffrey, Susan, "Catheter-based renal denervation reduces resistant hypertension", Medscape Medical News, Mar. 30, 2009, 4 pages.

Jokela, Kari, "Evaluation of compliance with SAR limits on the basis of external RFEM-field and induced current measurements", Non-Ionizing Radiation Laboratory STUK, Radiation and Nuclear Safety Authority (Finland), Feb. 14-16, 2007, 29 pages.

Kadziela, Jacek, "Evaluating Renal Denervation: A summary of ongoing and planned studies, as well as potential collateral benefits." Endovascular Today, Feb. 2012, 4 pages.

Rocha-Singh, Krishna J., "Renal Artery Denervation: A Brave New Frontier" Endovascular Today, Feb. 2012, 9 pages.

Rocha-Singh, Krishna J., "The Renal Renaissance", Endovascular Today, Feb. 2012, 1 page.

Krum, Henry, "Catheter-based renal sympathetic denervation for resistant hypertension: a multicentre safety and proof-of-principle cohort study", The Lancet, Apr. 11, 2009, 7 pages.

Krum, Henry, "Catheter-Base Renal Sympathetic Denervation in the Management of Resistant Hypertension", Center of Cardiovascular Research & Education in Therapeutics, Monash University, Melbourne, Australia, Nov. 16, 2012, 26 pages.

Kurzidim, Martin H., "Studies on the vasa vasorum of the human renal artery", Annals of Anatomy 1999, 5 pages.

Lerman, Lilach O., "Noninvasive Evaluation of a Novel Swine Model of Renal Artery Stenosis", Journal of the American Society of Nephrology, vol. 10, pp. 1455-1465, 1999, 11 pages.

Levin, David C., "New Curved Catheter for Renal Angioplasty", American Journal of Roentgenology, Feb. 1982, 2 pages.

Liu, Boshen, "Systemic and Renal-Specific Sympathoinhibition in Obesity Hypertension", Federation of American Societies for Experimental Biology Journal, 2011, 1 page.

Lohmeier, T.E., "Disparate Effects of Systemic and Renal-Specific Sympathoinhibition in Obesity Hypertension, " American Heart Association, Dec. 19, 2011, 1 page.

(56) References Cited

OTHER PUBLICATIONS

Mahfoud, Felix, "Is there a role for renal sympathetic denervation in the future treatment of resistant hypertension?" Future Medicine: Future Cardiology, 2011, 4 pages.
Accad, Michael, "Single-Step Renal Denervation with the OneShot(TM) Ablation System", Maya Medical, Inc. Created Nov. 16, 2012, 11 pages.
Medtronic, "Renal Devernation (RDN): Novel Catheter-Based Treatment for Hypertension", Medtronic, Inc., 2011, 5 pages.
Duck, Barbara, "Medtronic Acquires Hypertension Device Used to Deaden Nerves in the Kidney Area to Control Blood Pressure-Acquisitions Seen as Path Way for Growth", The Medical Quack, Nov. 24, 2010, 9 pages.
Merckel, Olivier, "E-Field Distribution modeling in a Homogeneous Phantom for a rapid SAR measurement", IEEE International Symposium on Electromagnetic Compatibility, May 2003, 4 pages.
Omary, R.A., "Magnetic Resonance-Guided Angioplasty of Renal Artery Stenosis in a Pig Model: A Feasibility Study", Departments of Radiology and Medical Physics, University of Wisconsin—Madison, Mar. 2000, 1 page.
Peyman, A., "Dielectric Properties of Tissues at Microwave Frequencies", Mobile Telecommunications Health Research Programme, Mar. 1, 2005, 50 pages.
"Renal Denervation Search Results", Clinical Trials.gov: A service of the U.S. National Institutes of Health, https://clinicaltrials.gov/ct2/results?term=renal+denervation, accessed Mar. 20, 2012, 2 pages.
"Renal sympathetic denervation in patients with treatment-resistant hypertension (The Symplicity HTN-2 Trial): a randomised controlled trial", The Lancet, vol. 376, Issue 9756, Dec. 4, 2010, 2 pages.
"Dielectric Constant, Strength, & Loss Tangent", RF Cafe, http://www.rfcafe.com/references/electrical/dielectric-constants-strengths.htm, accessed Jun. 14, 2012, 3 pages.
Riddle, Bill, "Complex Permittivity Measurements of Common Plastics Over Variable Temperatures", IEEE Transactions on Microwave Theory and Techniques, vol. 51, No. 3 Mar. 2003, 7 pages.
Scheinert, Prof. Dierk, "Renal Sympathetic Nerve Ablation for Resistant Hypertension", Center for Vascular Medicine, Angiology and Vascular Surgery—Park Hospital Leipzig, Germany, accessed Nov. 16, 2012, 22 pages.
Scheinert, Prof. Dierk, "Renal Denervation by RF-Ablation in Patients with Refractory Hypertension", Departments of Angiology—Park Hospital Leipzig, Germany, accessed Nov. 16, 2012, 15 pages.
Schlaich, Markus P., "Renal Sympathetic-Nerve Ablation for Uncontrolled Hypertension", New England Journal of Medicine, vol. 361, No. 9, Aug. 27, 2009, 3 pages.
Schlaich, Markus P., "Renal Denervation and Hypertension", American Journal of Hypertension, vol. 24, No. 6, Jun. 2011, 2 pages.
Schmidt, Andrei, "Endovascular Renal Artery Denervation for Treatment of Therapy-Refractory Hypertension", Center for Vascular Medicine, Angiology and Vascular Surgery, Park Hospital and Heartcenter Leipzig, Germany, accessed Apr. 10, 2011, 21 pages.
Sievert, FL, "Radiofrequency Ablation of the Renal Arteries for Treatment of Severe Hypertension: A New Treatment Concept", Innovations in Cardiovascular Interventions, Dec. 6, 2009, 60 pages.
Singh, Vibhuti N., "Renal Artery Angioplasty", Medscape Reference: Drugs, Diseases & Procedures, http://emedicine.medscape.com/article/1817671-overview, Jan. 26, 2012, 15 pages.
Sobotka, Paul A., "Sympatho-Renal Axis and Sympathetic Hyperactivity", Medtronic Coporation 2011, 19 pages.
Sripairojthikoon, W., "Renal nerve contribution to NaCl-exacerbated hypertension in spontaneously hypertensive rats", Hypertension: Journal of the American Heart Association, 1989, vol. 14, 8 pages.
Stuart, Mary, "Renal Denervation: Device Market's Gold Rush", Start-Up Apr. 2012, vol. 17, No. 4, 13 pages.
Thompson, Keith A., "Drug-resistant Hypertension: Is Renal Sympathetic Denervation the Answer?", Current Cardiology Reports, vol. 13, Jan. 19, 2011, 3 pages.
"Top 10 Innovations for 2012", Cleveland Clinic, http://innovations.clevelandclinic.org/Summit/Top-10-Medical-Innovations/Top-10-for-2012/1-Catheter-Based-Renal-Denervation-to-Control-Res.aspx, 2012, 2 pages.
Papademetriou, Vasilios, "Renal Sympathetic Denervation for the Treatment of Difficult-to-Control or Resistant Hypertension", International Journal of Hypertension, vol. 2011, 8 pages.

* cited by examiner

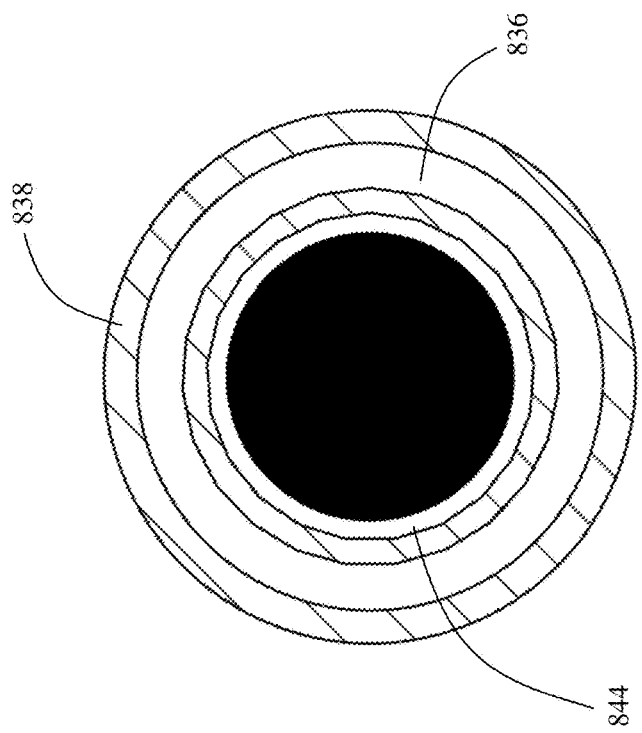

COOLED MICROWAVE DENERVATION CATHETER CONFIGURATION AND METHOD

CROSS-REFERENCE TO RELATED APPLICATION(S)

This application is a divisional of U.S. application Ser. No. 14/605,556 filed Jan. 26, 2015 for "Cooled Microwave Denervation Catheter Configuration" by Eric N. Rudie, Philip J. Haarstad, and Stanley E. Kluge, which in turn claims the benefit of U.S. Provisional Application No. 61/931,420 filed Jan. 24, 2014 for "Cooled Microwave Denervation Catheter Configuration" by E. Rudie et al., which is incorporated by reference herein in its entirety.

BACKGROUND

The present disclosure is directed to catheter configurations for cooled microwave denervation.

SUMMARY

A cooled microwave denervation catheter includes a catheter body having at least one fluid passage and an interior lumen therein, the interior lumen having a first portion in a first axial region, a second portion in a second axial region, and a taper between the first portion and the second portion, the second portion having a smaller diameter than the first portion. A balloon communicates with the at least one fluid passage to receive cooling fluid for inflating the balloon into a shape that surrounds the catheter body at the first portion of the interior lumen, the cooling fluid having a temperature that is less than basal body temperature. A microwave antenna catheter is configured to be inserted into the interior lumen of the catheter body, the microwave antenna catheter including a coaxial cable and a microwave antenna connectable to a microwave generator to supply power to the microwave antenna to cause microwave energy to be emitted from the microwave antenna. A distal end of the microwave antenna catheter is configured to engage the taper between the first portion and the second portion of the catheter body upon insertion into the interior lumen, thereby positioning the microwave antenna in the first portion of the interior lumen.

BRIEF DESCRIPTION OF THE DRAWINGS

FIG. 24 depicts an alternate cross section for the shaft of the catheter shown in FIGS. 21-23.

DETAILED DESCRIPTION

The present disclosure is directed to catheter configurations for cooled microwave denervation. In certain embodiments, denervation is performed by positioning a catheter carrying a microwave antenna within a body vessel/lumen adjacent targeted nerves being treated, circulating cooling fluid around the microwave antenna in thermal contact with the inner wall of the body vessel/lumen, supplying power to the microwave antenna to cause microwave energy to be emitted from the microwave antenna toward the targeted nerves. The power supplied to the microwave antenna and the cooling fluid circulated around the microwave antenna are controlled to cause the targeted nerves to be heated to a temperature sufficient to cause thermal damage while the wall of the body vessel/lumen is maintained at a temperature where thermal damage does not occur. Various embodiments of cooled microwave denervation catheter configurations are described herein and shown in FIGS. 1-24.

Figure 1:
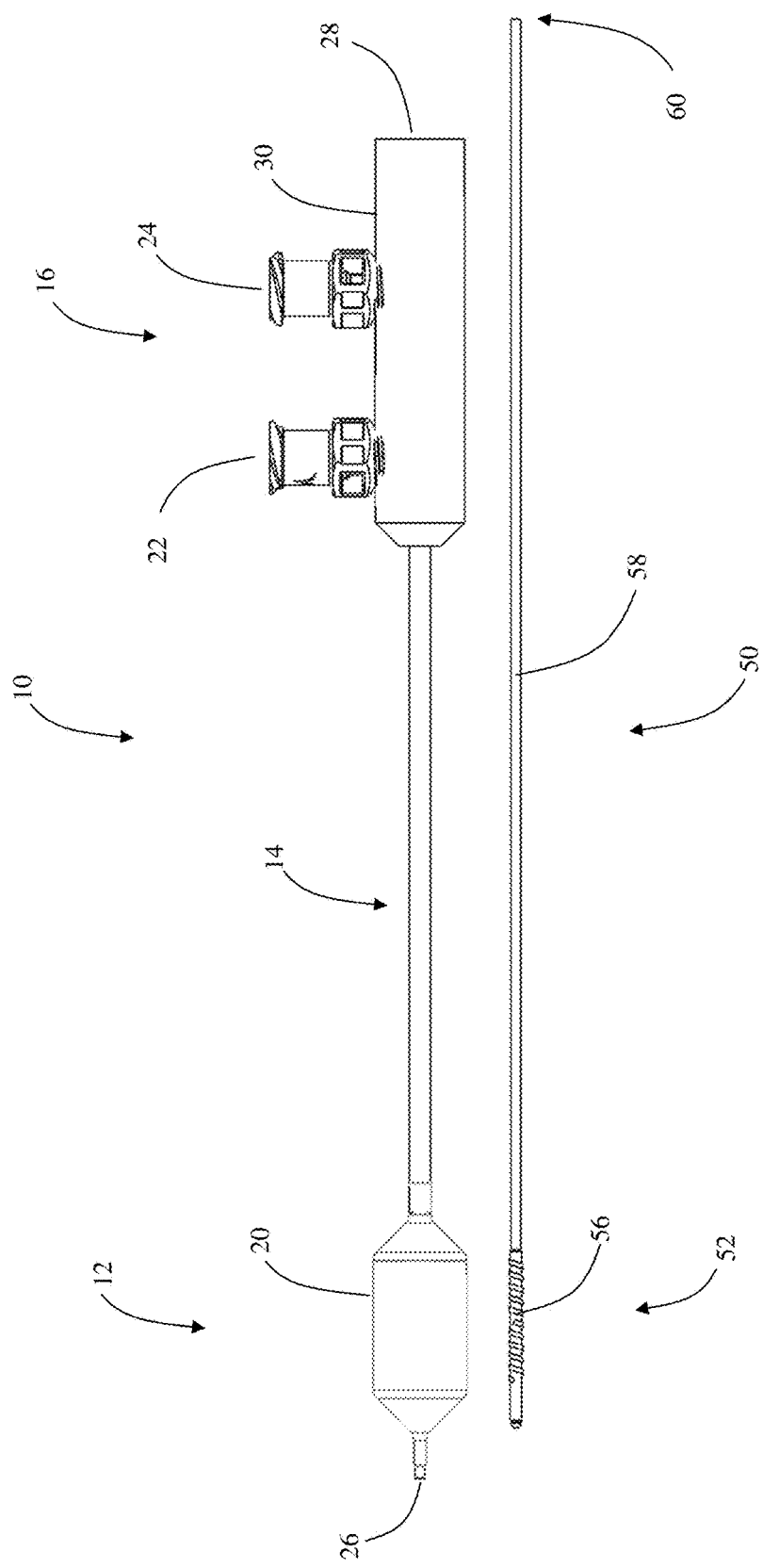
FIG. 1 depicts a cooled microwave denervation catheter embodiment wherein the treatment catheter is separated into a first catheter and an antenna catheter.

FIG. 1 depicts an embodiment wherein the treatment catheter is separated into two catheters. The first catheter 10 has distal end 12, middle portion 14 and proximal end 16. Distal end 12 includes cooling balloon 20 adapted to communicate with lumens for inflow and outflow. The lumens exit the catheter through inlet connector 22 and outlet connector 24 on manifold 30. Catheter 10 also contains lumen 44 (shown in FIG. 2) extending from tip port 26 to proximal port 28 on manifold 30 through which a guide wire or antenna catheter 50 may be inserted. The second catheter, antenna catheter 50, contains microwave antenna 56 connected through coaxial cable 58 to a suitable connector, 60, such as a subminiature version A (SMA) connector, connected on the proximal end 54 of antenna catheter 50. Antenna 56 may be any embodiment as described in U.S. application Ser. No. 14/032,013 filed Sep. 19, 2013, which is hereby incorporated by reference.

Figure 2:
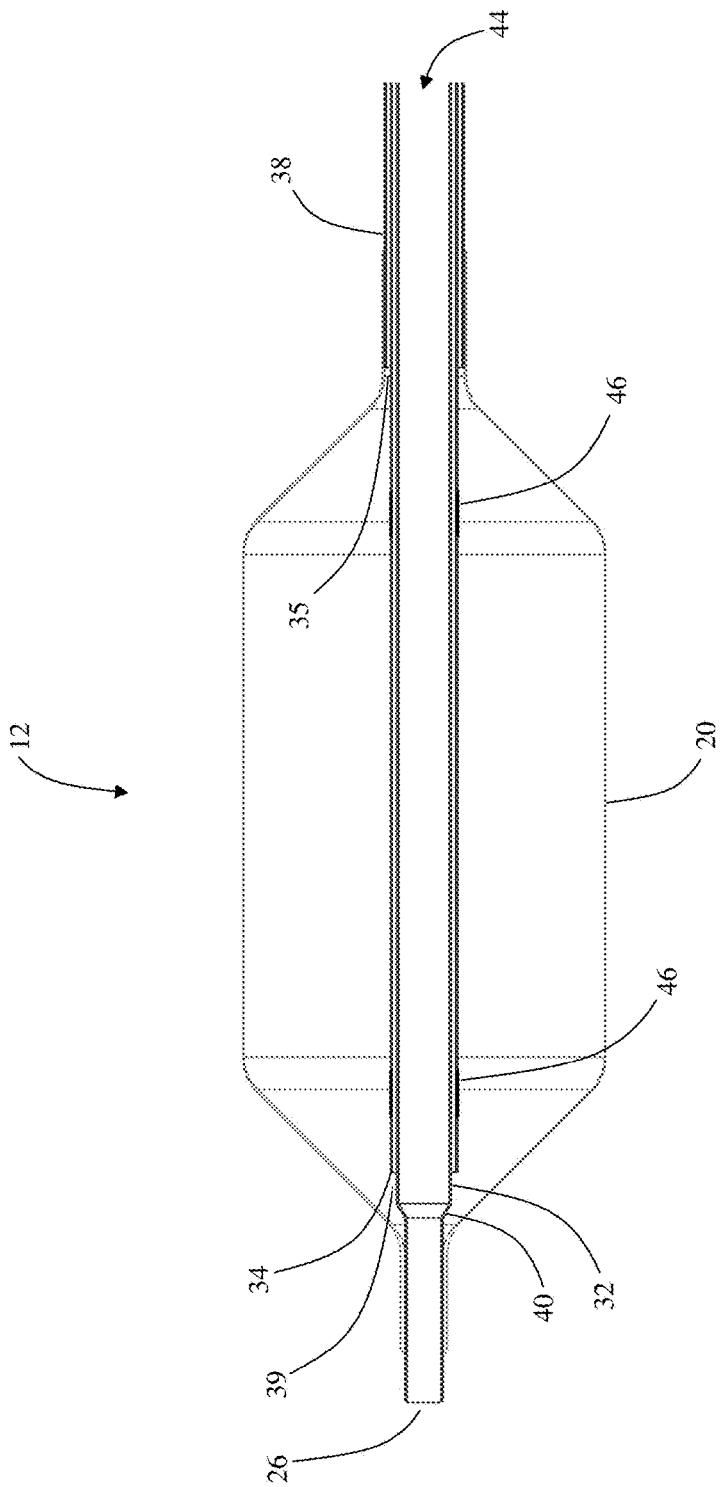
FIG. 2 is an enlarged view of the distal end of the first catheter shown in FIG. 1.

FIG. 2 is an enlarged view of distal end 12 of catheter 10. Inner tube member 32 forms lumen 44 within which antenna catheter 50 or a guide wire may be inserted. Taper 40 serves to transition the diameter of lumen 44 to match tip orifice 26. Taper 40 also serves to align antenna catheter 50 correctly within cooling balloon 20. A cooling lumen 37 (shown in FIGS. 5 and 6) is formed in the annular space between tube member 32 and tube member 34. Coolant flows into lumen 37 and exits into balloon 20 through proximal exchange port 35 formed when outer tube member 38 ends. Inner tube member 34 extends to the distal end of balloon 20 and forms distal coolant exchange port 39 into which coolant flows and into lumen 36 formed by the annular space between inner and outer tube member. Distal exchange port 39 is located near the distal end of balloon 20 to ensure that coolant is circulated within substantially the entire length of cooling balloon 20. Tube member 38 serves as the outer wall of catheter 10 and forms a cooling lumen in the annular space between tube member 34 and tube member 38. Radio opaque markers 46 are positioned about tube member 34 and are used to facilitate location of catheter 10 within renal artery under fluoroscopic guidance.

Figure 3:
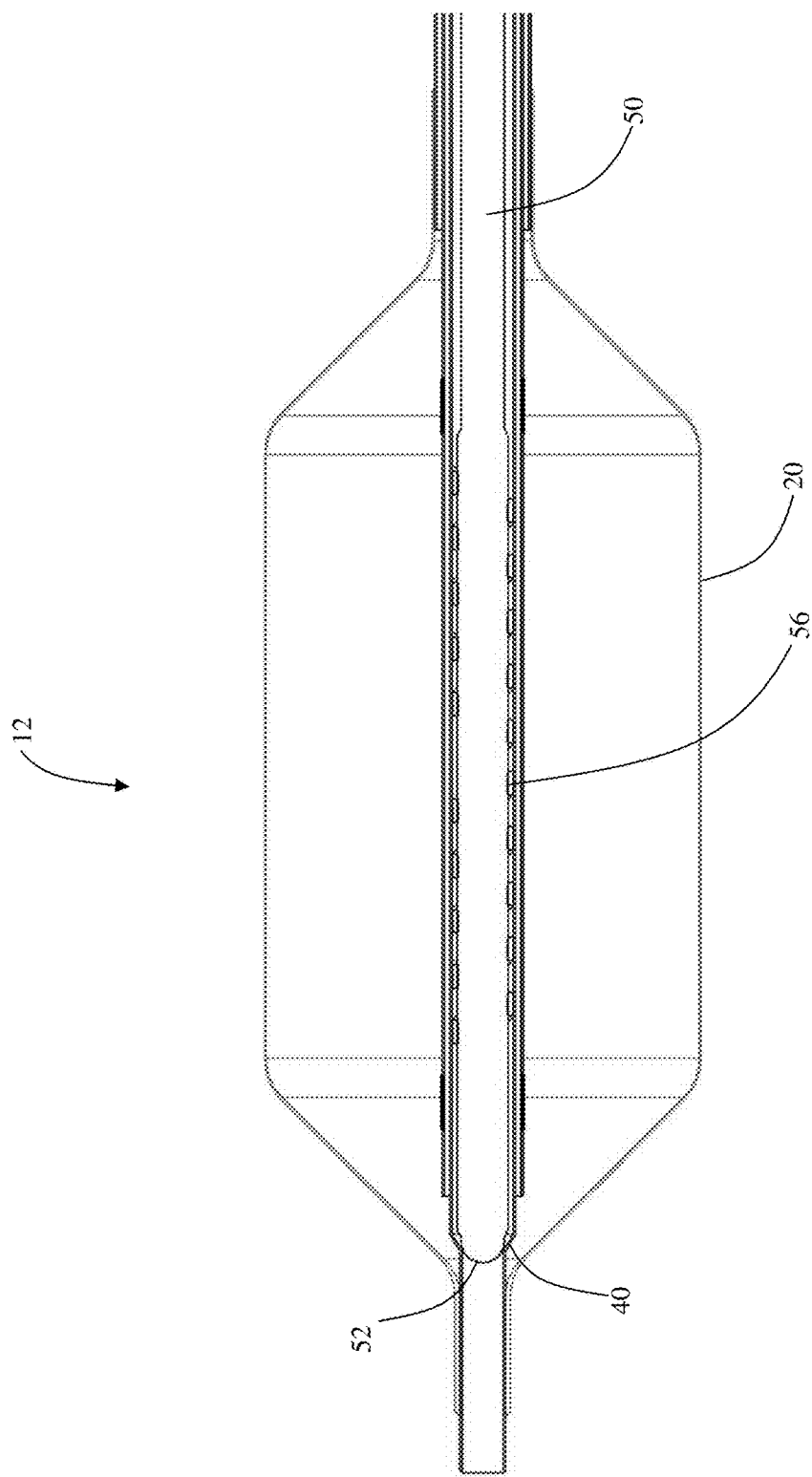
FIG. 3 is an enlarged view of the distal end of the first catheter shown in FIG. 1, with the antenna catheter positioned within a lumen and advanced until the distal end of the antenna catheter engages a taper.

FIG. 3 is an enlarged view of distal end 12 of catheter 10 with antenna catheter 50 positioned within lumen 44 and advanced until distal end 52 of antenna catheter 50 engages taper 40. Antenna 56 is shown correctly positioned within balloon 20.

Figure 4:
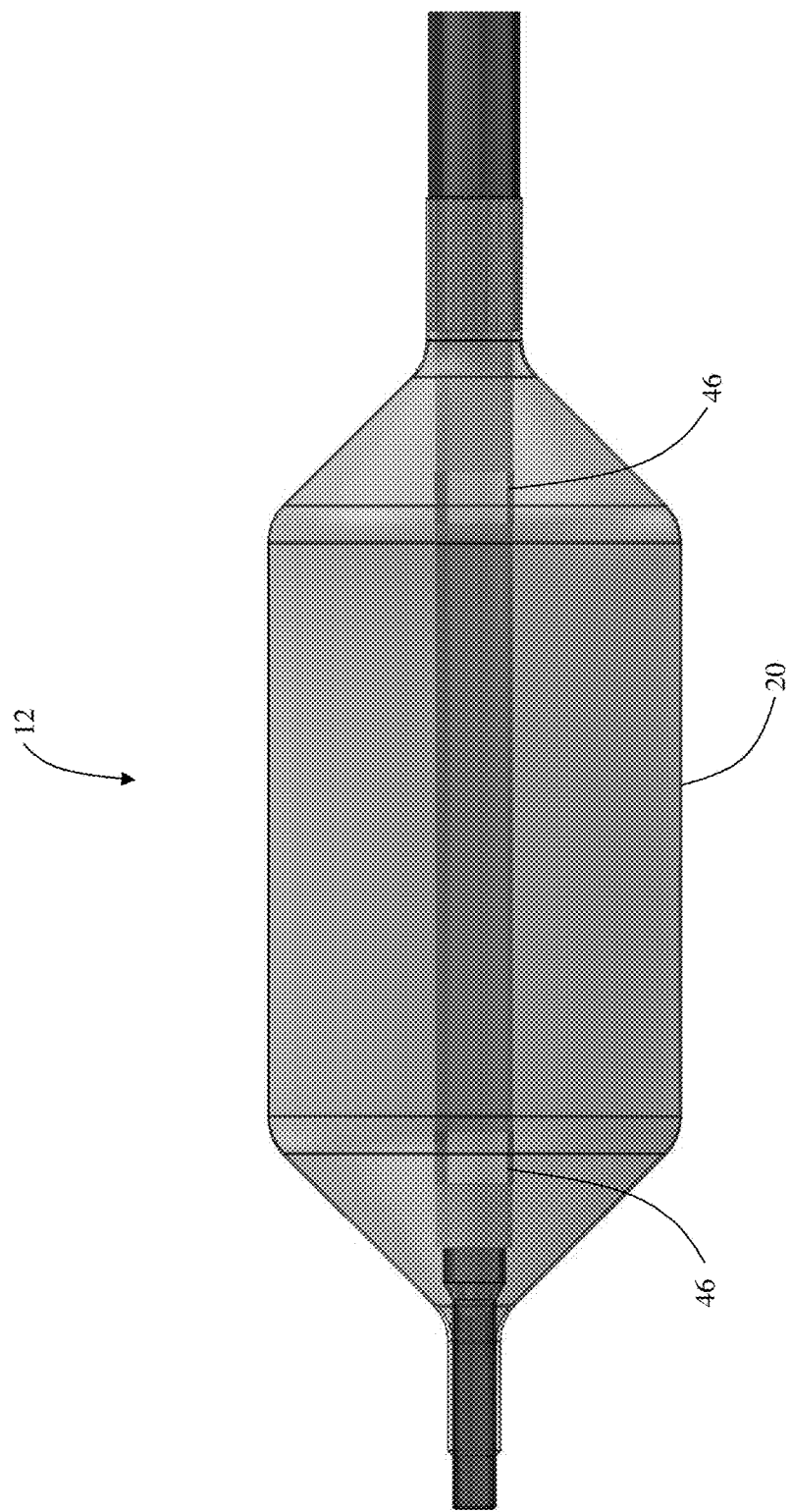
FIG. 4 is an enlarged and shaded view of the distal end of the first catheter shown in FIG. 1, with the antenna catheter placed within the first catheter.

FIG. 4 is an enlarged and shaded view of distal end 12 of catheter 10 with antenna catheter 50 placed within catheter 10. Shading of balloon 20 and catheter tubing helps to visualize the tubing walls.

Figure 5:
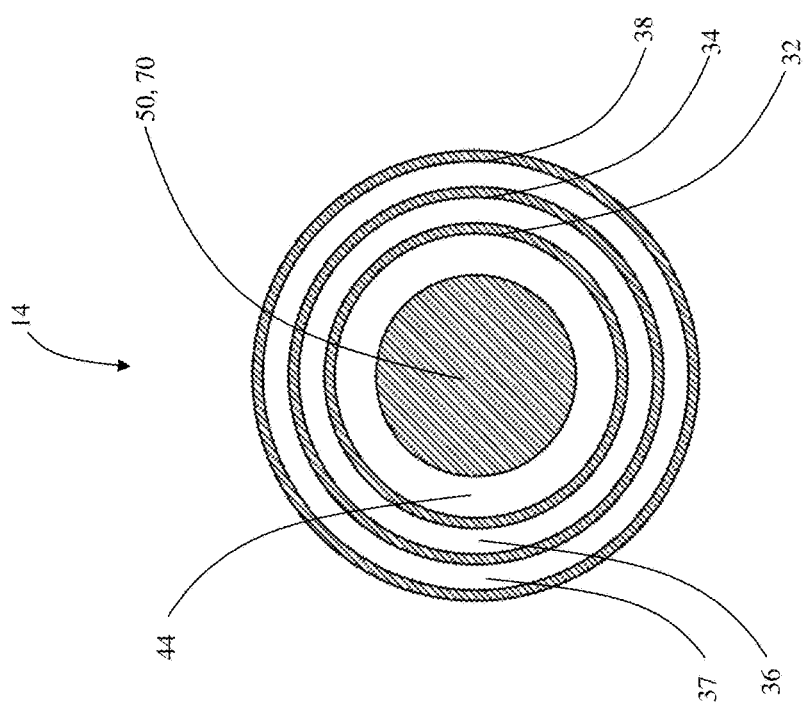
FIG. 5 is an enlarged cross section of the middle section of the first catheter shown in FIG. 1.

FIG. 5 is an enlarged cross section of the middle section 14 of catheter 10. Coolant flows in the annular spaces 37 and 36 between tube members 32, 34 and 38. The inner lumen 44, central to tube member 32, may contain guide wire 70 to facilitate introduction, or antenna catheter 50 for treatment. The guide wire 70 and antenna catheter 50 are each represented by the same circular cross section. However, they may be of different diameters and only one of them will be present at a time.

Figure 6:
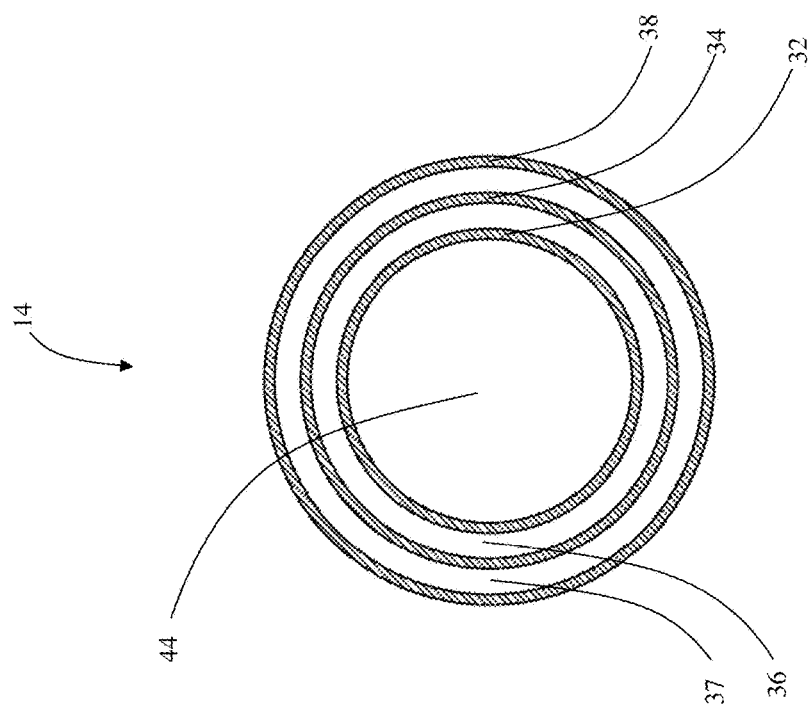
FIG. 6 is an enlarged cross section of a portion of the middle section of the first catheter shown in FIG. 1.

FIG. 6 is an enlarged cross section of the middle of section 14 of catheter 10. However, this drawing has inner lumen 44 empty. Central lumen 44, tubing members 32, 34 and 38 and annular space 37 and 36 are the same as in FIG. 5.

Figure 7:
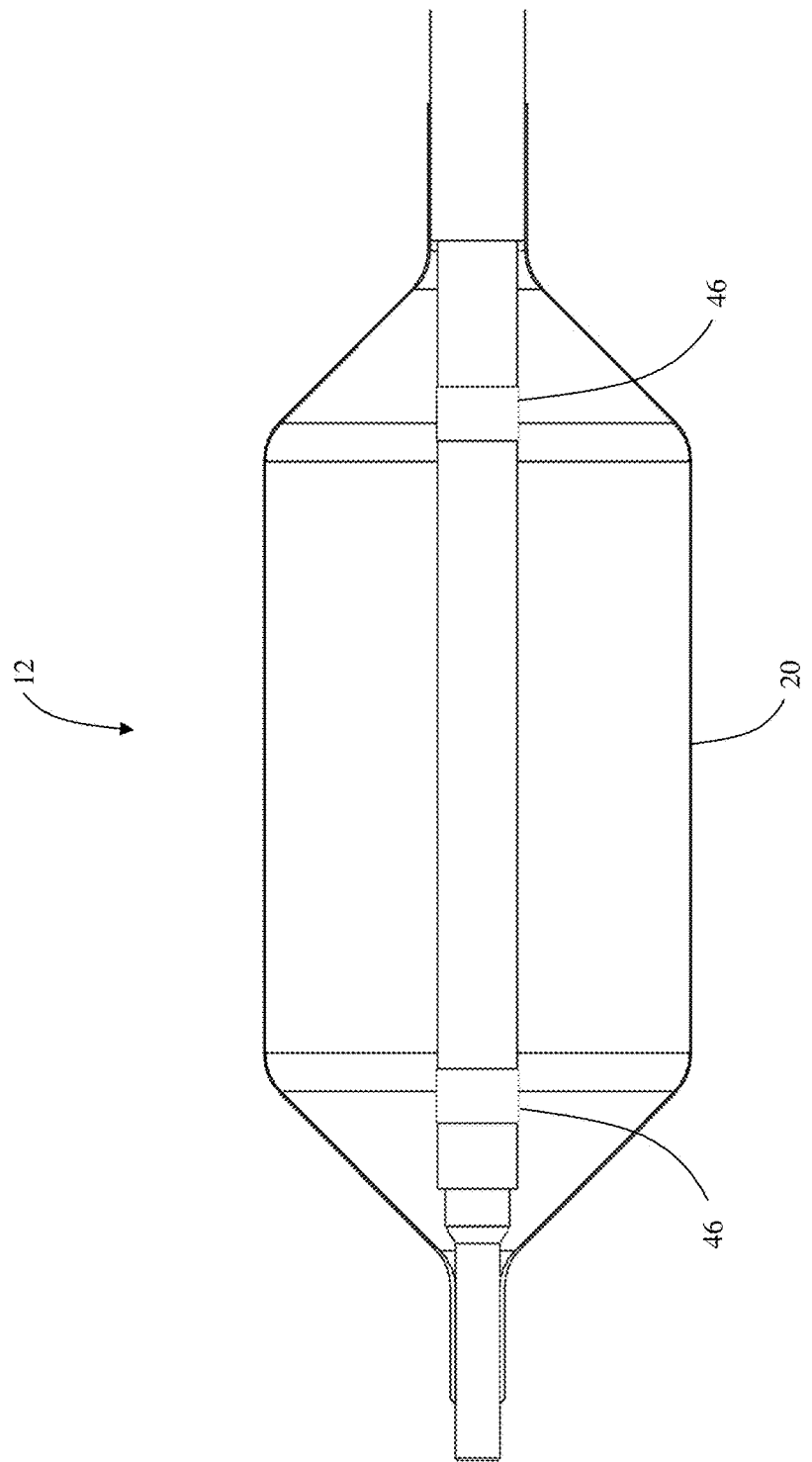
FIG. 7 is an enlarged cross section of the distal end of the first catheter shown in FIG. 1.

FIG. 7 is an enlarged cross section of distal end 12 of catheter 10. Radio opaque markers 46 are more clearly visible within balloon 20 and are used to guide location of balloon 20 within the treatment location.

In an exemplary operation of the embodiment represented in FIGS. 1-7, catheter 10 is advanced over a guide wire 70 to the desired treatment location. Radio opaque marker bands 46 help the operator position the cooling balloon catheter 10 in the desired location via fluoroscopy. The guide wire 70 is then removed, leaving the cooling balloon catheter 10 in place. The antenna catheter 50 is then inserted into the central lumen 44 of catheter 10 and advanced until distal end 52 of microwave catheter 50 engages taper 40 and thereby locates antenna 56 within balloon 20 in order to precisely target the treatment location. Denervation treatment is then executed by applying coolant flow and microwave power in accordance with the U.S. application Ser. No. 14/032,013 referenced above. Once the treatment period is complete, coolant is discontinued, balloon 20 is deflated, and both the cooling balloon catheter 10 and microwave catheter 50 are removed.

It can be appreciated that one advantage of this embodiment is that the number of lumens required to perform the treatment is reduced. This is a result of the guide wire 70 and antenna catheter 50 sharing the same lumen at different times during the procedure. Additionally, the lumen size available to the guide wire is much larger. Typical guide wire diameters for vascular interventions may be 0.014", 0.018", 0.035" and 0.038". Since the diameter of the antenna catheter 10 in a preferred embodiment is greater than 0.038", central lumen 44 may in some embodiments accommodate guide wire sizes as large as 0.038. These larger guide wire sizes can be an advantage in providing support to the delivery of the cooling balloon catheter in comparison with the use of 0.014" or 0.018" guidewires.

Embodiment DNX-001 B

Figure 8:
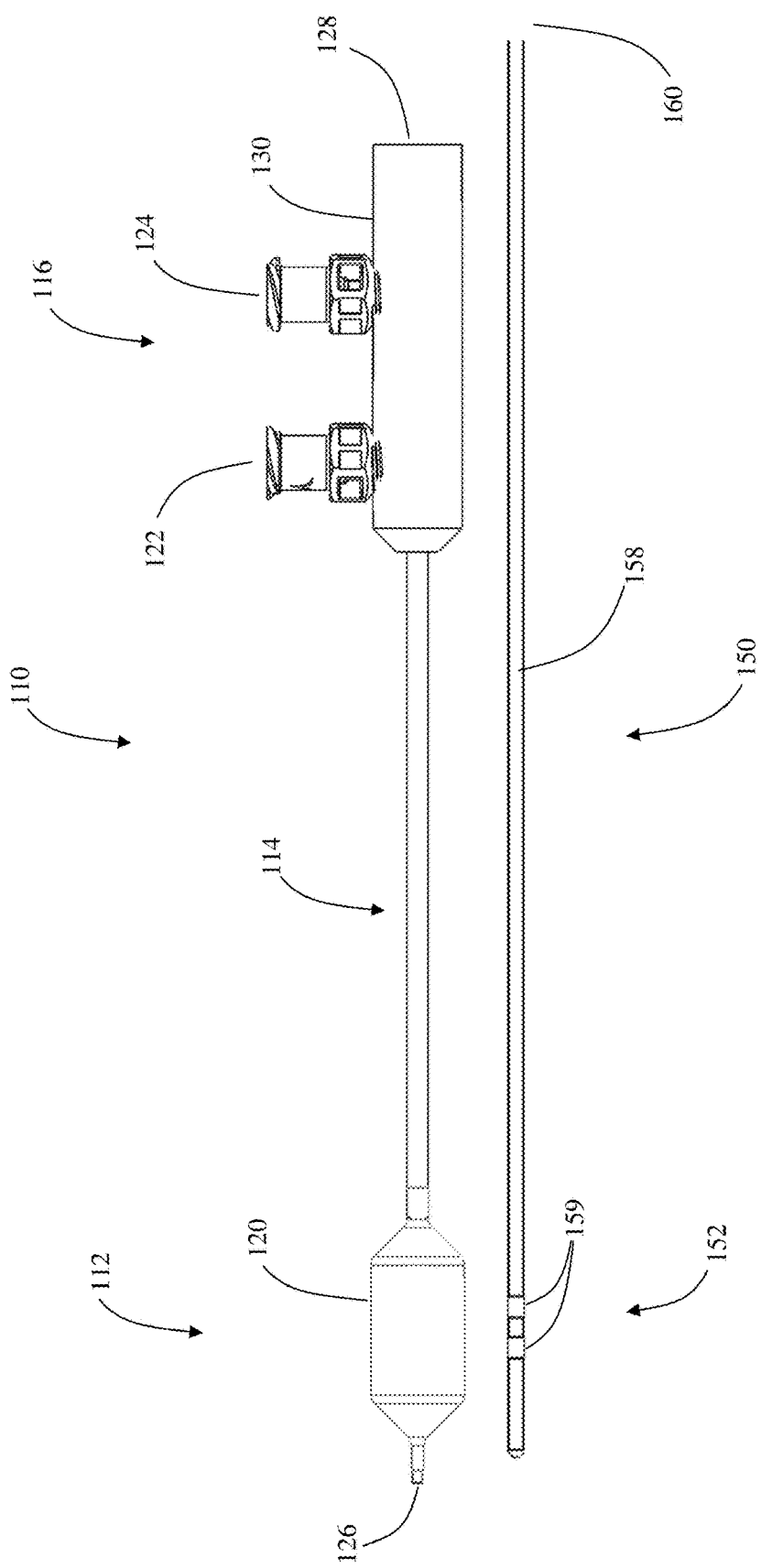
FIG. 8 depicts another cooled microwave denervation catheter embodiment in which the treatment catheter is separated into a first catheter and a second catheter.

FIG. 8 depicts another embodiment in which the treatment catheter is separated into two catheters. The first catheter 110 is a cooling balloon catheter that contains a microwave antenna within the cooling balloon 120 in the distal portion 112. Connection manifold 130 is located on proximal portion 116 of catheter 110. Cooling connections 122 and 124 communicate through manifold 130 to cooling lumens within catheter 110 to the distal section 112. A guide wire may be inserted into orifice 128 and advanced through catheter 110, exiting orifice at tip 126 to facilitate placement of catheter 110 within a body at the desired treatment location.

Figure 9:
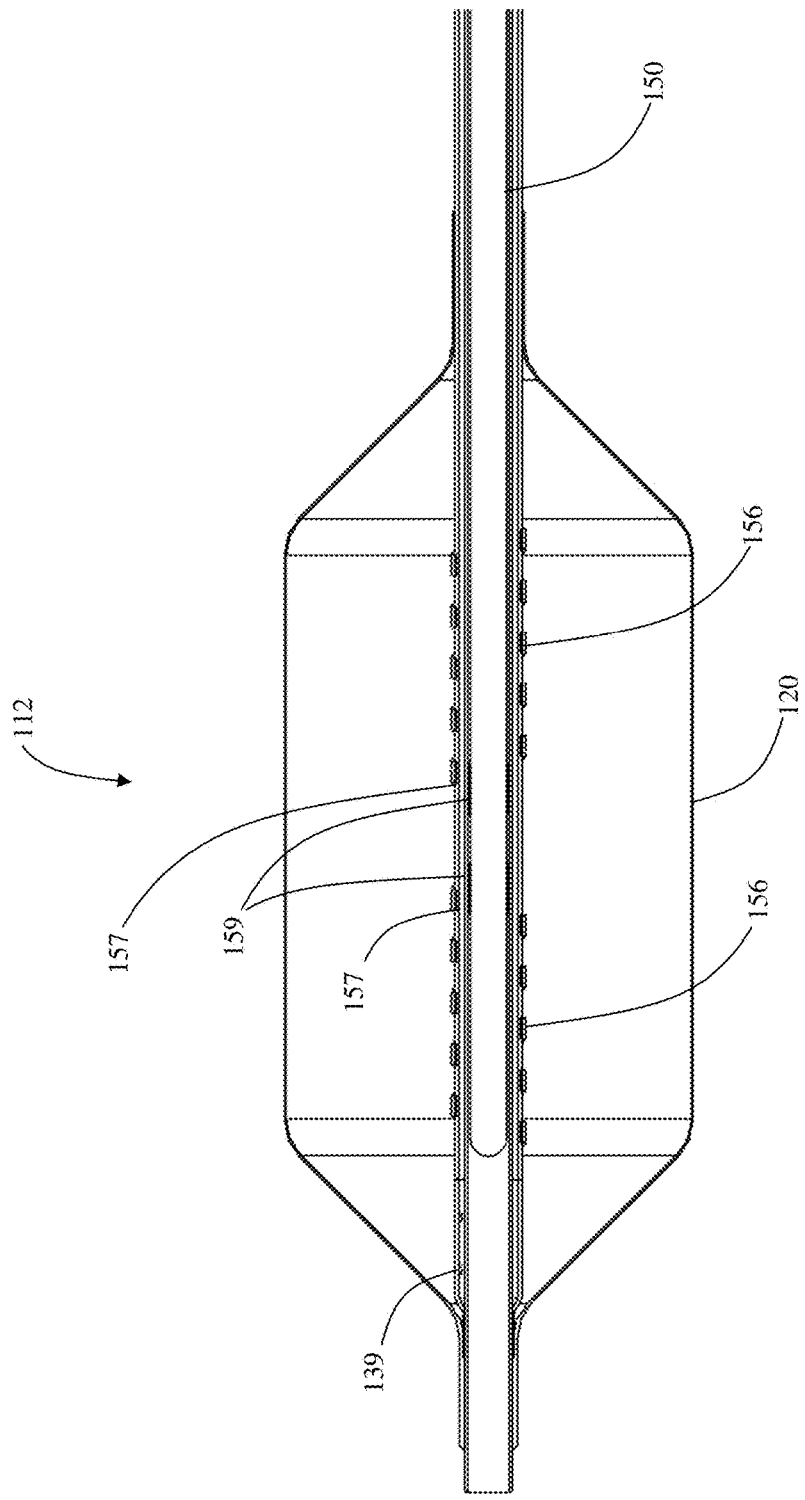
FIG. 9 depicts the distal portion of the first catheter shown in FIG. 8 with the second catheter placed within it.

Once catheter 110 is in the desired location, the guide wire may be removed and catheter 150 may be inserted into orifice 128. Catheter 150 contains coaxial cable 158 extending from contacts 159 located at distal portion 152 to microwave connector 160. Microwave connector 160 may be an SMA or other appropriate connector. Once catheter 150 is properly positioned within catheter 110, contacts 159 on catheter 150 mate with corresponding contacts 157 (shown in FIG. 9) located within catheter 110 to enable microwave excitation of antenna 156 (FIG. 9). Coolant may be circulated through lumens within 110 so that balloon 120 may be inflated and denervation treatment may commence. Once the treatment period is complete the cooling balloon with antenna and coaxial cable are removed.

FIG. 9 depicts distal portion 112 of catheter 110 with catheter 150 placed within. Antenna 156 is located within balloon 120 and is electrically connected to catheter 150 by contacts 157 and 159 to enable it to be energized by microwave current applied to connector 160 (FIG. 8) located on the proximal end of catheter 150. Coolant is circulated through manifold 130, lumens 136 and 137 and into balloon 120 through proximal and distal ports 135 and 139. Balloon 120 is inflated by this circulating coolant so that the body lumen containing treatment catheter 110 may be protected. With catheter 150 placed within catheter 110 and connected as described, denervation treatment may commence. Once the treatment period is complete the cooling balloon with antenna and coaxial cable are removed. Radio opaque marker bands may be used to help visualize location of balloon 120 within the body lumen adjacent to the region requiring treatment.

Figure 10:
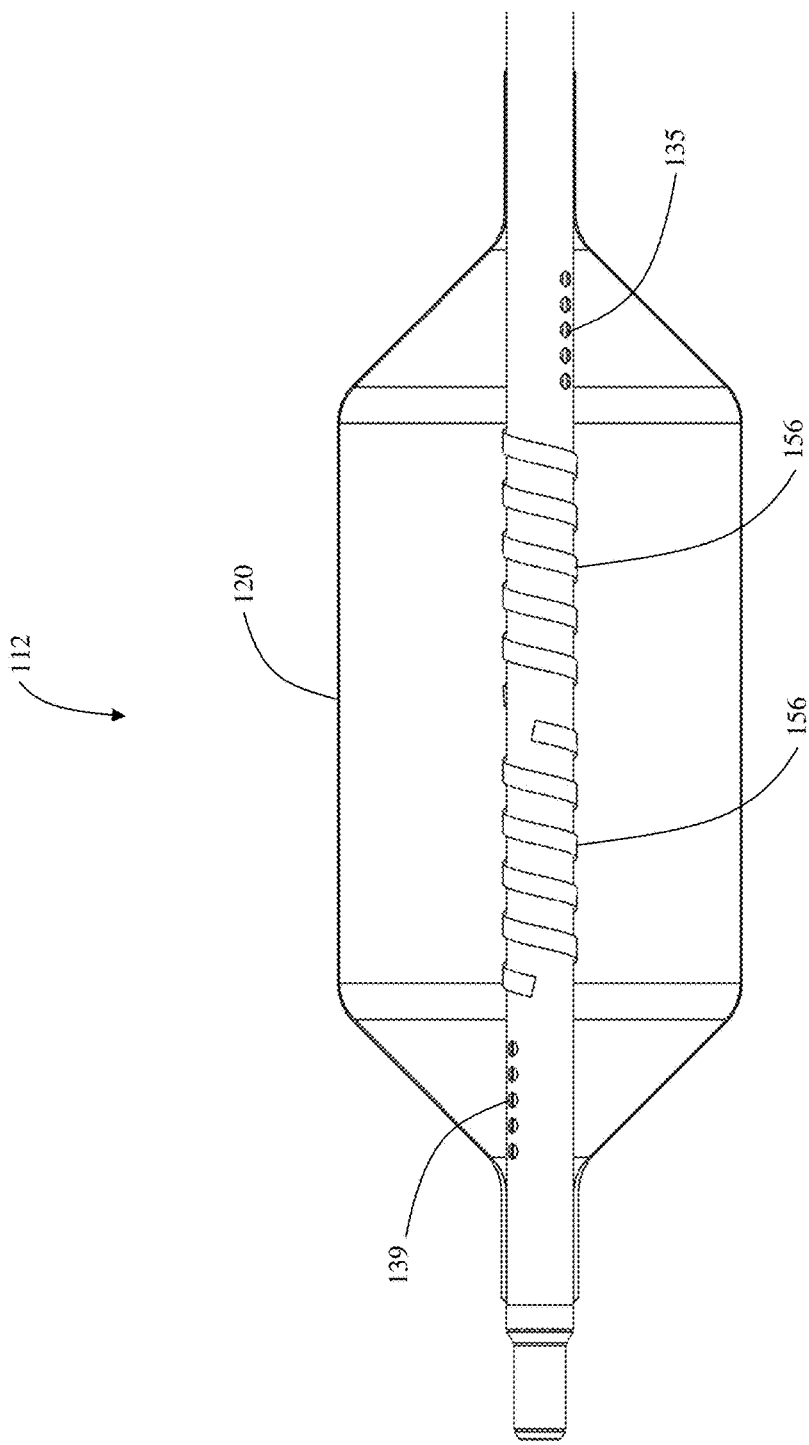
FIG. 10 is another view of the distal end of the first catheter shown in FIG. 8.
Figure 11:
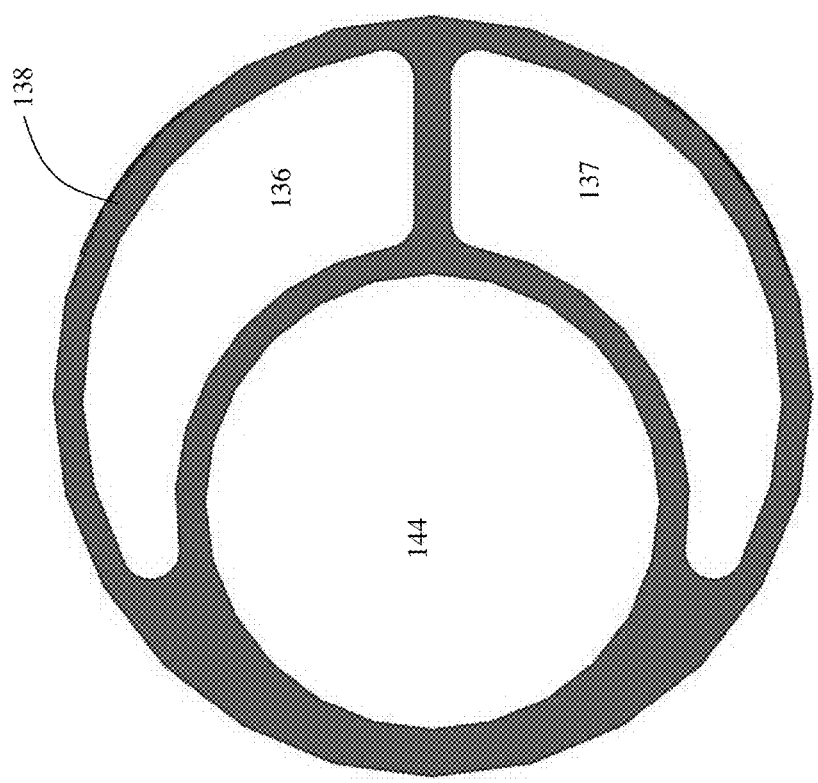
FIG. 11 is a cross section of multi lumen tubing showing cooling lumens and also a guide wire/antenna cable lumen.

FIG. 10 is another view of distal end 112 of catheter 110. Antenna 156 is clearly located on multi lumen tube 138 (shown in cross-section in FIG. 11). Proximal and distal coolant ports 135 and 139 are more clearly visible as apertures in multi lumen tube 138 that enable communication with lumens 136 and 137 (FIG. 11). Radio opaque marker bands may be used to help visualize location of balloon 120 within the body lumen adjacent to the region requiring treatment.

FIG. 11 is a cross section of multi lumen tubing 138 showing cooling lumens 136 and 137 and also guide wire/antenna cable lumen 144.

Figure 12:
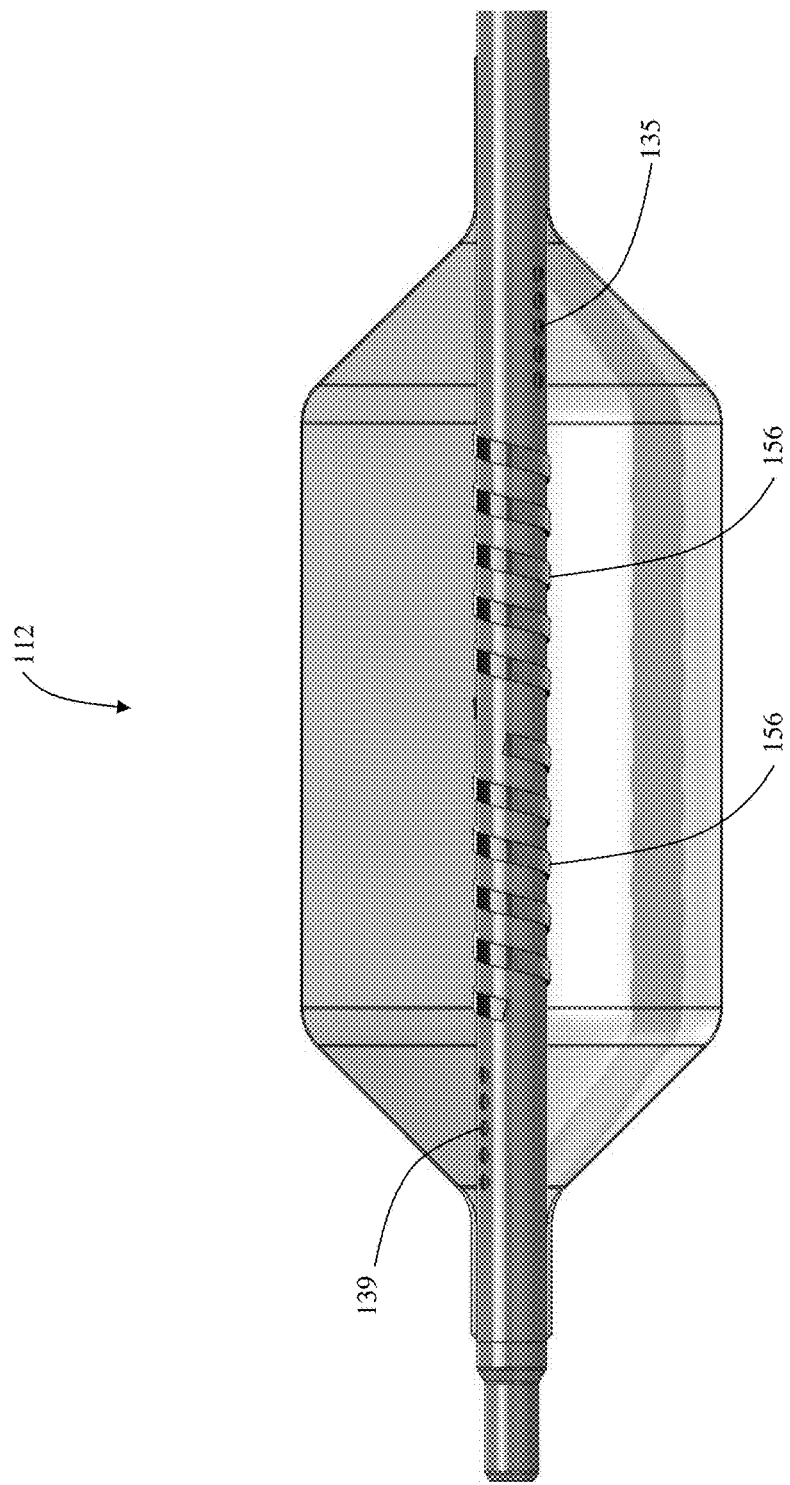
FIG. 12 is a shaded drawing of the distal end of the first catheter shown in FIG. 8.

FIG. 12 is a shaded drawing of distal end 112 of catheter 110. The location of antenna 156, and cooling ports 135 and 139 are visible.

In some embodiments, for optimal microwave energy transmission it may be desirable for the diameter of the microwave antenna to be significantly larger than the commonly used 0.035" or 0.038" guidewires. Mounting this larger antenna inside the balloon allows the lumen for guidewire and coaxial cable to be suited for 0.035" or 0.038" guidewire. Marker bands may not be necessary in this embodiment if the antenna is significantly radiopaque.

Shaft Embodiments

Figure 13:
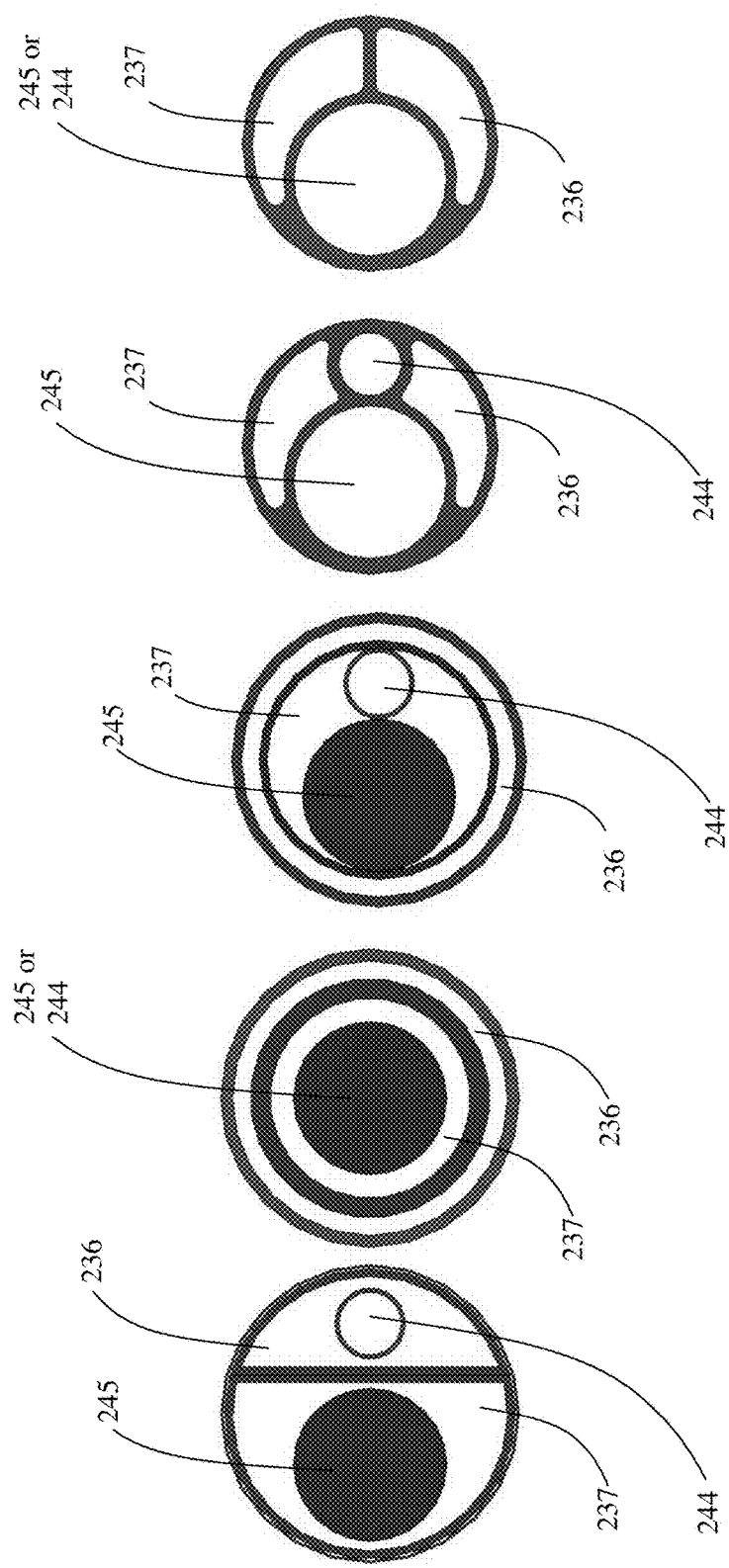
FIG. 13 depicts alternate cooled microwave denervation catheter shaft embodiments that can be used in conjunction with any embodiment that requires an antenna cable lumen, inflow cooling fluid lumen, outflow cooling fluid lumen, and a guide wire lumen or a subset of these.

FIG. 13 depicts alternate shaft embodiments that can be used in conjunction with any embodiment that requires an antenna cable lumen 245, inflow cooling fluid lumen 236, outflow cooling fluid lumen 237, and a guide wire lumen 244 or a subset of these.

Embodiment DNX-005

Figure 14:
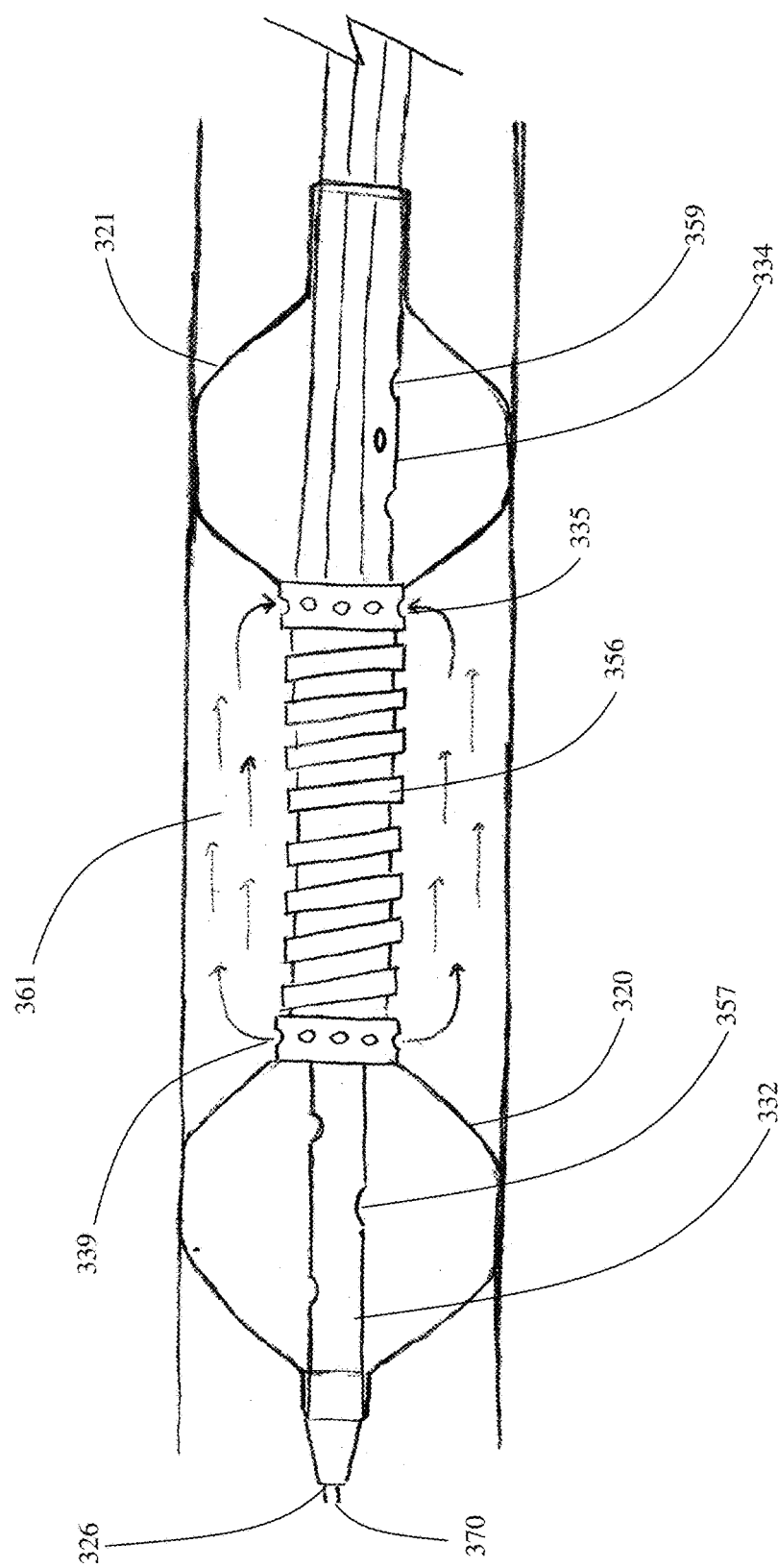
FIG. 14 depicts a cooled microwave denervation catheter embodiment in which two balloons are used to occlude the body lumen, center the antenna within the body lumen, and create a chamber within which coolant is circulated.

FIG. 14 depicts an embodiment in which two balloons are used to occlude the body lumen, center the antenna within the body lumen, and create a chamber within which coolant is circulated. The catheter of this embodiment is advanced over guide wire 370 exiting the device at orifice 326 until proper position within the body lumen is achieved. Distal occlusion balloon 320 is attached to multi lumen tube 332 and is inflated through port 357. Proximal occlusion balloon 321 is attached to outer multi lumen tube 334 and is inflated through port 359. Both balloons center antenna 356 within chamber 361 formed by occluding balloons 320 and 321. Coolant is circulated through lumens within multi lumen tube 334 and enters chamber 361 through port 339. Coolant exits chamber 361 through port 335 and returns through lumens within multi lumen tube 334. Cooling of the body lumen is accomplished by direct heat exchange between coolant within chamber 361 and the body lumen. Microwave antenna 356 may then be energized to accomplish denervation.

Embodiment DNX-007

Figure 15:
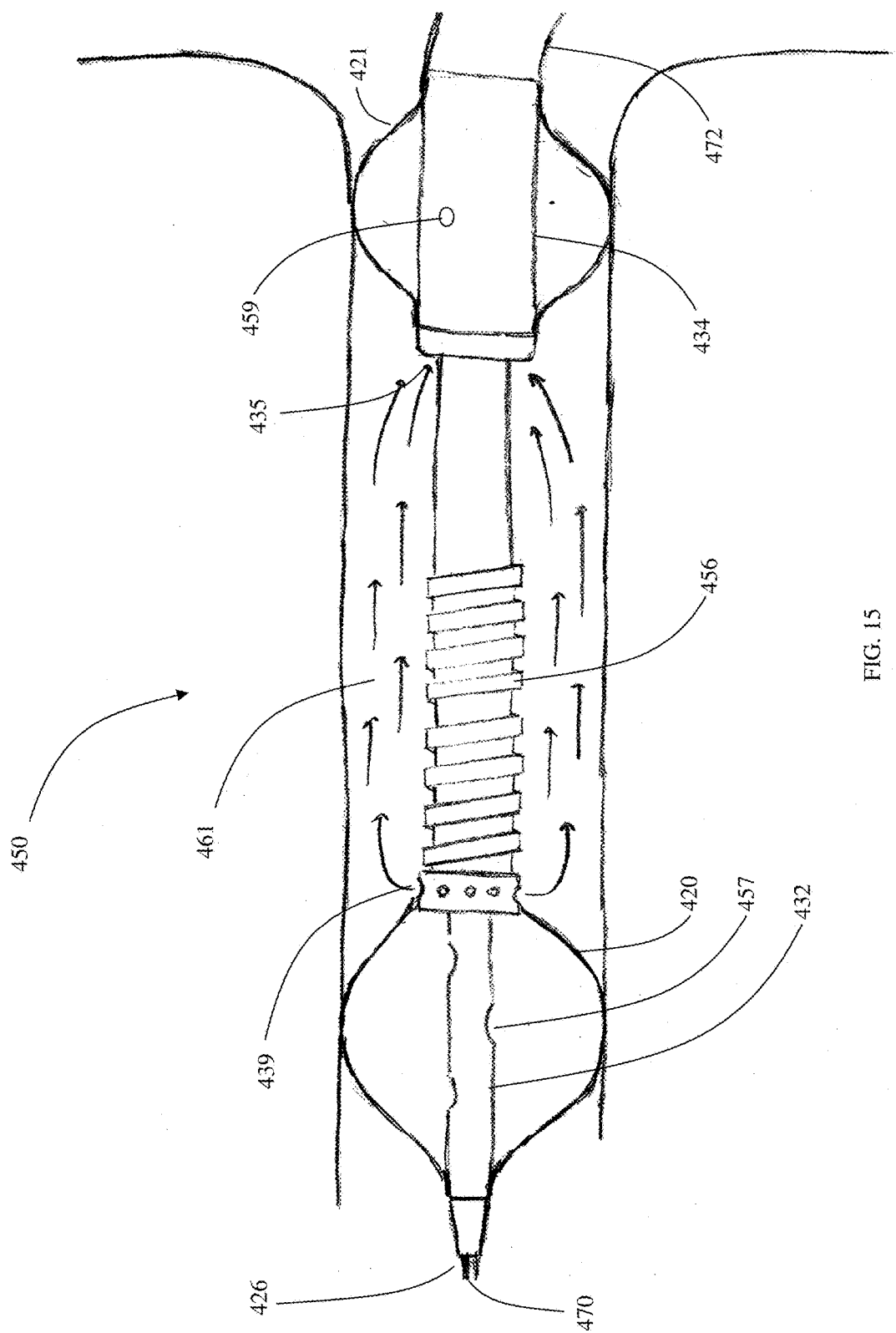
FIG. 15 depicts a cooled microwave denervation catheter embodiment in which a guide catheter is equipped with an occluding/locating balloon inflated through a port via a lumen within a multi lumen tube, to locate guide catheter just proximal to a treatment site adjacent to the body lumen.

FIG. 15 depicts an embodiment in which guide catheter 472 is equipped with occluding/locating balloon 421 inflated through port 459 via a lumen within multi lumen tube 434, to locate guide catheter just proximal to a treatment site adjacent to the body lumen. Antenna catheter 450 is advanced over guide wire 470 exiting an orifice at tip 426, through guide catheter 472, until it is positioned within the body lumen at the treatment site. Proximal balloon 420 is inflated through port 457 via a lumen within multi lumen tube 432 and thereby centers antenna 456 within chamber 461 formed by balloons 420 and 421. Coolant may then be circulated through a lumen within multi lumen tube 432, through distal coolant port 439 and into chamber 461. The body lumen is cooled by direct contact with coolant along chamber 461. Coolant enters port 435 formed by the annular space between catheter 450 and the inner lumen of guide catheter 472. Since the cooling fluid is returned thru the guide catheter lumen by entering orifice 435 formed by the guide catheter inner lumen and the antenna catheter 450 outer shaft; catheter 450 does not require an outflow lumen. Therefore, the available cross sectional area of 450 may be allocated to a single, higher flow lumen.

In operation, the guide catheter 472 is first positioned just proximal to the treatment site using standard interventional techniques. Once the guide catheter is in position, the balloon 421 on the guide catheter can be inflated via port 459 to occlude the body lumen. This balloon can also help anchor the guide catheter in the body lumen for the entire procedure. Next, treatment catheter 450 is advanced through guide catheter 472 and into the desired body lumen to the desired treatment location. Distal balloon 420 may then be inflated via port 457. Coolant circulation may then be initiated, thus circulating coolant within chamber 461 from distal port 439 to proximal port 435 formed by the annulus between the outer shaft of 450 and the inner lumen of guide catheter 472. Cooling fluid will make direct contact with artery wall for optimal heat transfer effect.

Embodiment DNX-008

Figure 16:
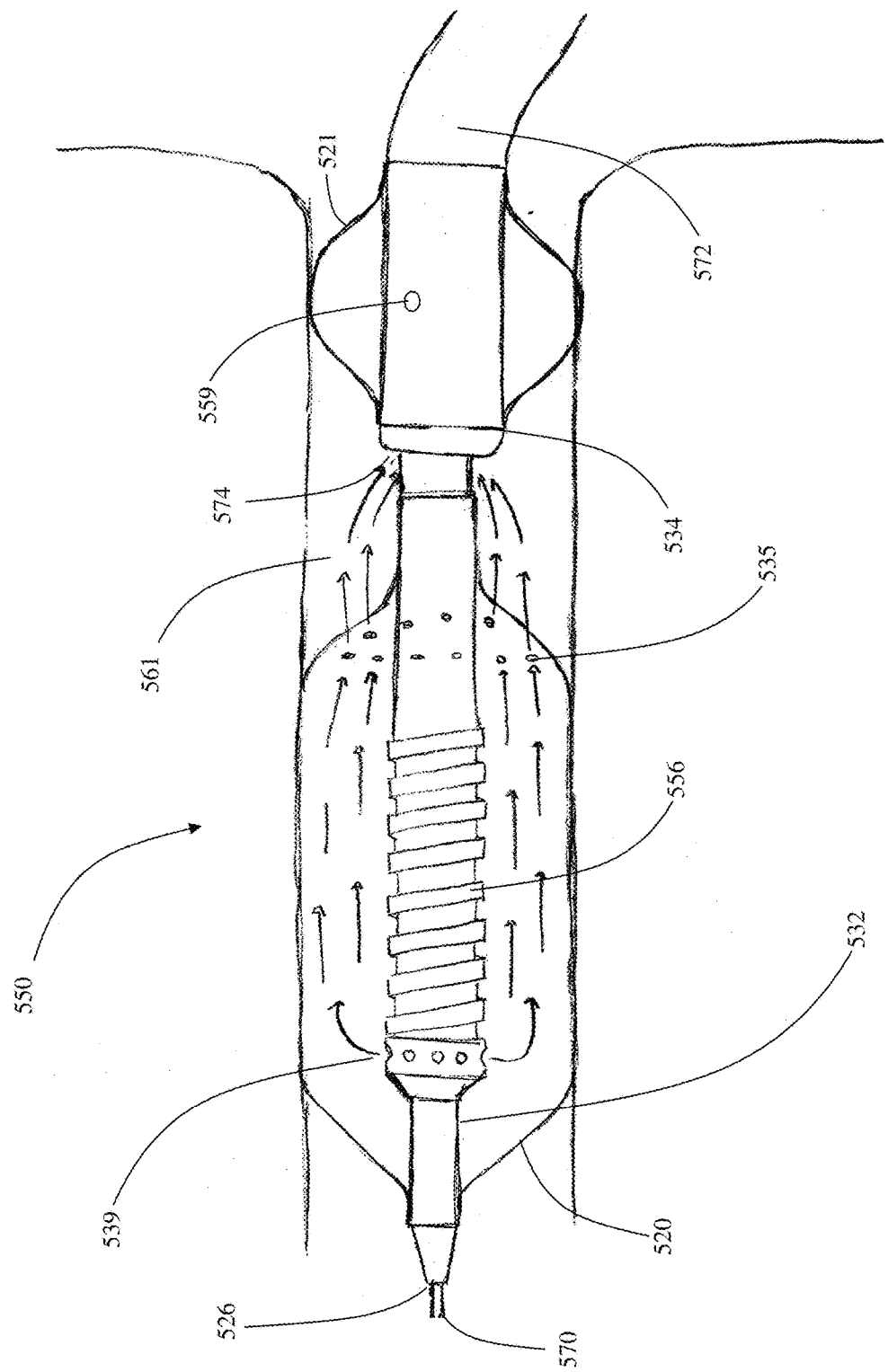
FIG. 16 depicts a dual balloon cooled microwave denervation catheter embodiment wherein the treatment catheter includes a microwave antenna mounted within a balloon.

FIG. 16 depicts a dual balloon embodiment wherein the treatment catheter 550 includes microwave antenna 556 mounted within balloon 520. A second balloon 521 is mounted on guide catheter 572. On the proximal taper of the treatment catheter balloon 520 are apertures 535, which are small enough to allow the balloon to inflate during the treatment period but large enough to allow cooling fluid to leak therethrough under pressure. Accordingly, coolant enters balloon 521 through distal port 539 into balloon 520 where it circulates and cools the body lumen. Coolant exits balloon 520 through apertures 535 at the proximal taper and flows into chamber 561 formed by balloons 520 and 521. Coolant enters port 574 formed by the annular space between the outer shaft of catheter 550 and the inner lumen of guide catheter 572 where it is captured externally. Coolant balloon 520 also centers antenna 556 within the body lumen adjacent to the region be treated.

In operation, guide catheter 571 is first positioned in the body lumen using standard interventional techniques. Once the guide catheter is in position, balloon 521 is inflated via port 559 to locate the guide catheter and occlude the body lumen. Next, treatment catheter 550 is advanced through the guide catheter 572 into the body lumen and to the desired treatment location. Once there, balloon 520, is inflated by circulating cooling fluid as described above. Antenna 556 is then energized as described in U.S. application Ser. No. 14/032,013. Once treatment is finished, balloon 520 is deflated by discontinuing coolant circulation. Balloon 521 may then be deflated and catheter 550 and guide wire 572 may be repositioned to an additional treatment site or removed.

Figure 17:
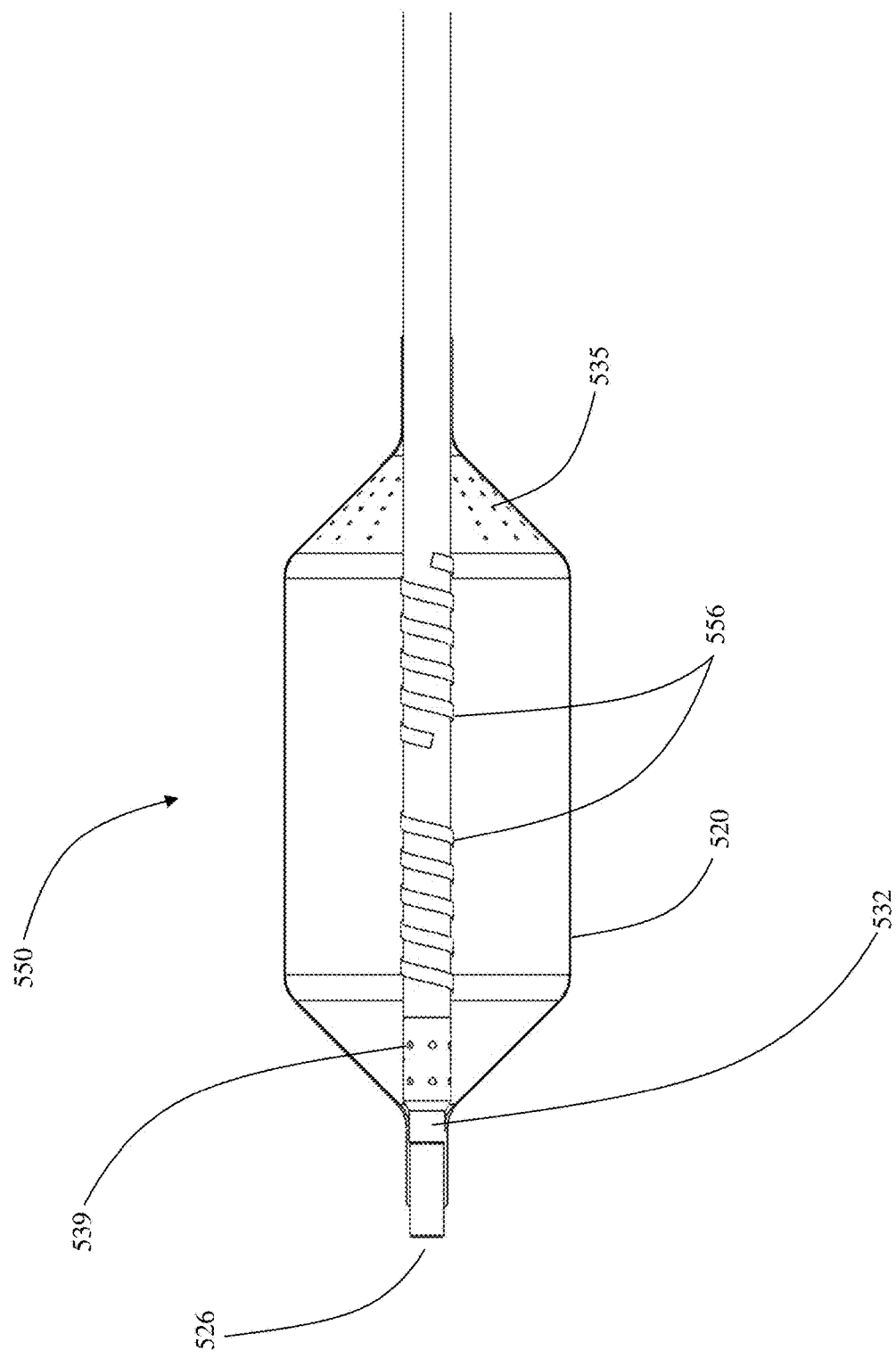
FIG. 17 is another view of the catheter shown in FIG. 16.
Figure 18:
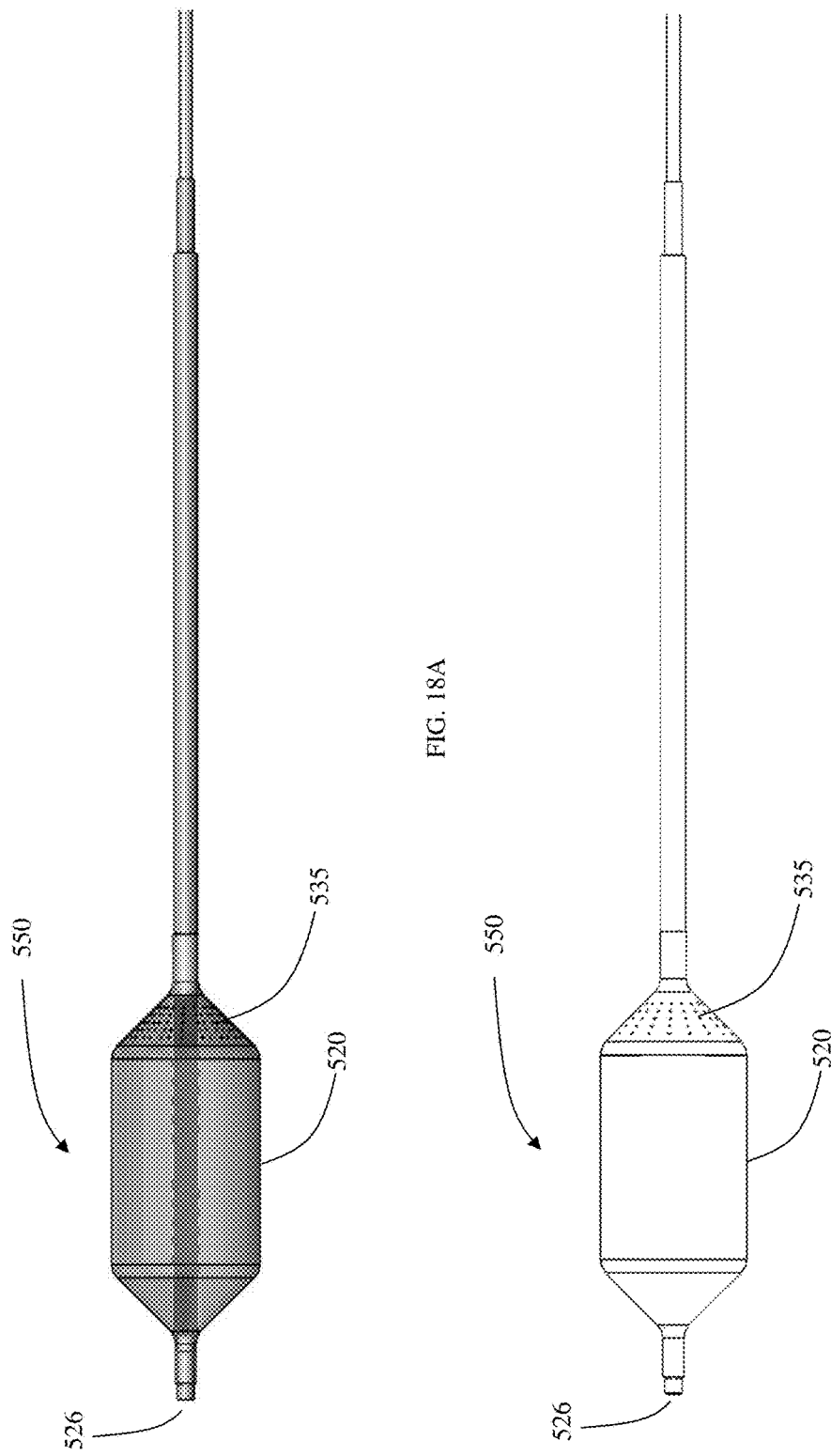
FIG. 18A and FIG. 18B are alternate views of the catheter shown in FIG. 16.

FIG. 17 is another view of catheter 550. Antenna 556 is mounted on catheter shaft 532 within balloon 520. Apertures on catheter shaft 532 form distal cooling port 539 that permits coolant to flow from the cooling lumen within shaft 523 and into balloon 520. Proximal cooling port 535 allows coolant to flow out of balloon 520. Orifice 526 located on distal tip of shaft 532 allows the guide wire to exit catheter 550. Radio opaque markers may be utilized if needed.

Embodiment DNX-008 B

FIG. 18A and FIG. 18B are alternate views of catheter 550. Catheter 550 may be placed into the desired body lumen using only guide wire guidance through port at distal tip 526, or it may be placed with a standard, single lumen guide catheter, or a combination of both. In this case, coolant exits port 535 formed by many small apertures sized to maintain balloon pressure under active coolant flow, and flows directly into the body lumen. The coolant flow rate and treatment duration are such that a relatively modest amount of coolant is discharged into the body lumen of the patient and is not harmful. This embodiment is similar to DNX-008 described above, but does not include a balloon on the distal end of the guide catheter. In the case of the body lumen being an artery or vein, cooling fluid will be discharged into the blood stream of the patient. A blood compatible fluid like sterile dextrose may be used in some embodiments.

Embodiment DNX-008 C

Figure 19:
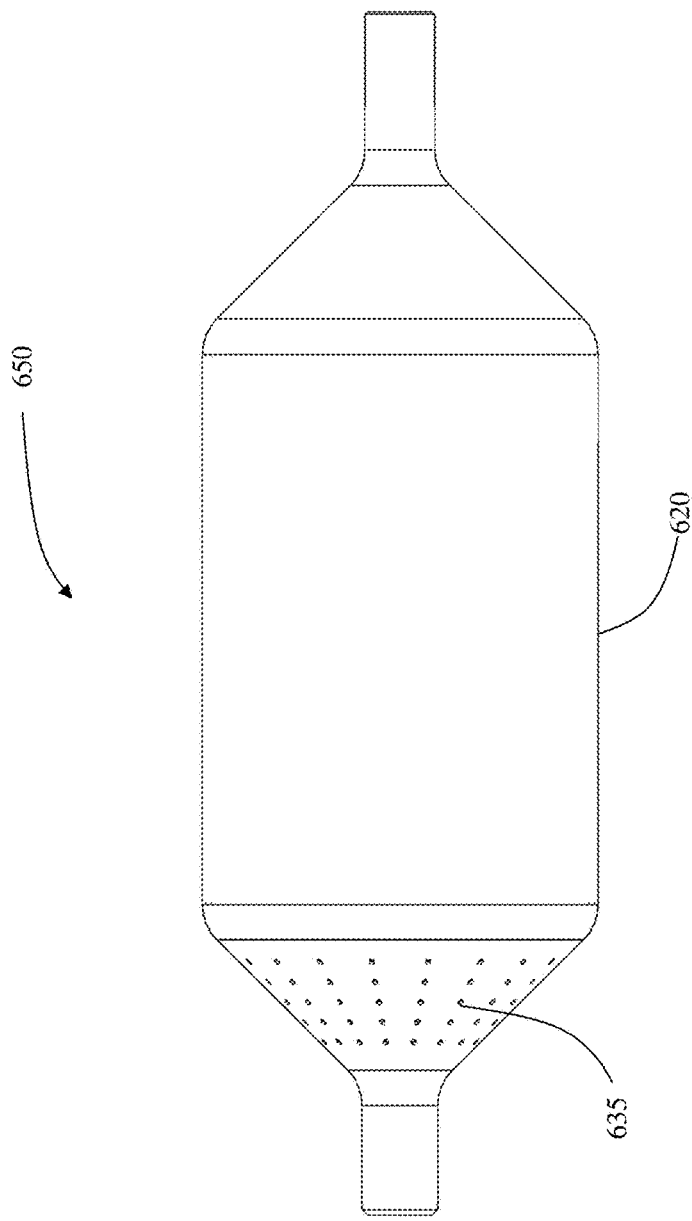
FIG. 19 depicts the distal end of another embodiment of a cooled microwave denervation catheter.

FIG. 19 depicts distal end of catheter 650. Balloon 620 functions as generally described in the preceding embodiments, except that apertures 635 in balloon 620 serve to discharge cooling fluid into the body lumen on the distal side of balloon 620. Depending on the body lumen being treated, it may be preferable to discharge cooling fluid either proximal or distal to cooling balloon 620. A coolant port may be located in the distal end of balloon 620 so that coolant along body lumen is optimally moving in order that cooling may be most effectively accomplished.

Embodiment DNX-008 D

Figure 20:
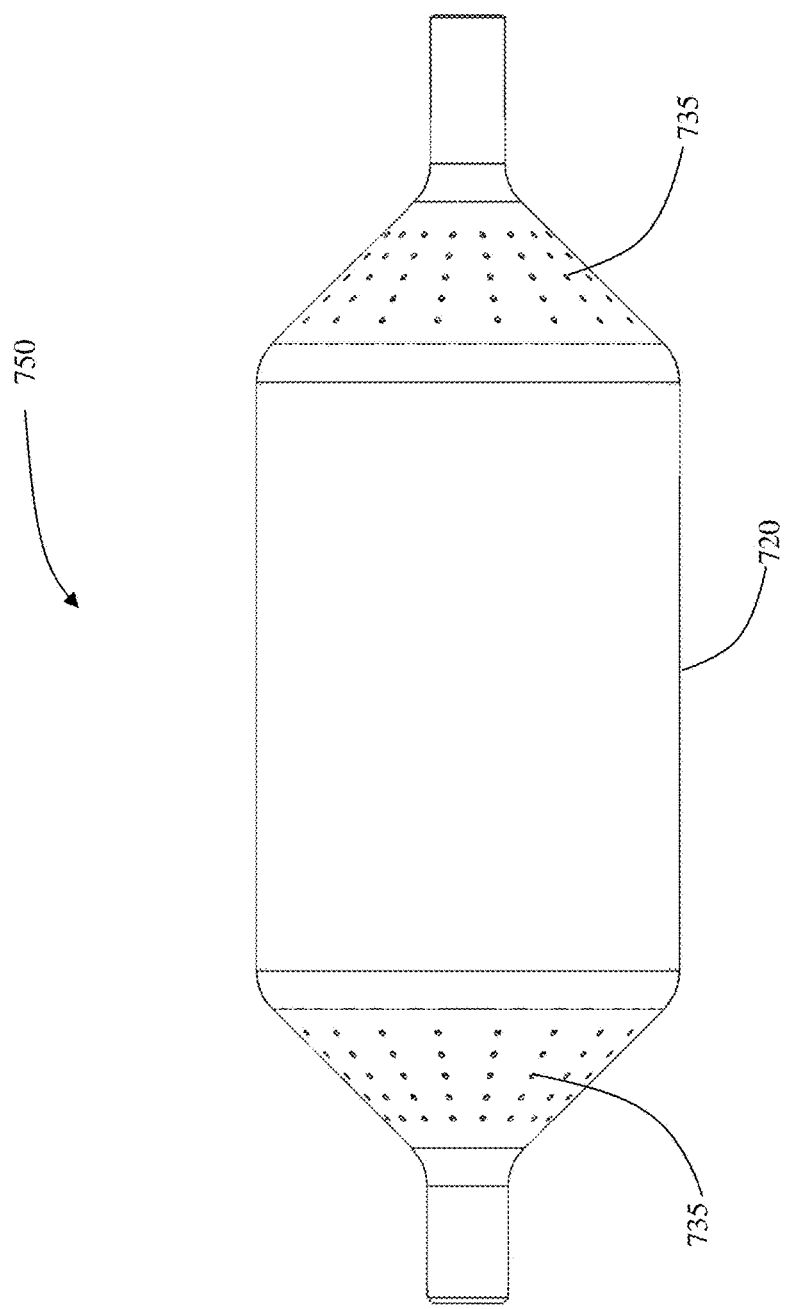
FIG. 20 depicts the distal end of a further embodiment of a cooled microwave denervation catheter.

FIG. 20 depicts distal end of catheter 750. Balloon 720 functions as generally described in the preceding embodiments, except apertures 735 in balloon 720 serve to discharge coolant both proximal and distal to balloon 720. Depending on the body lumen being treated, it may be preferable to discharge a smaller volume of fluid on each side of inflated balloon 720. In this case, a coolant port may be located in the center of the balloon or in another location to optimize cooling flow adjacent the body lumen being cooled.

Embodiment DNX-012

Figure 21:
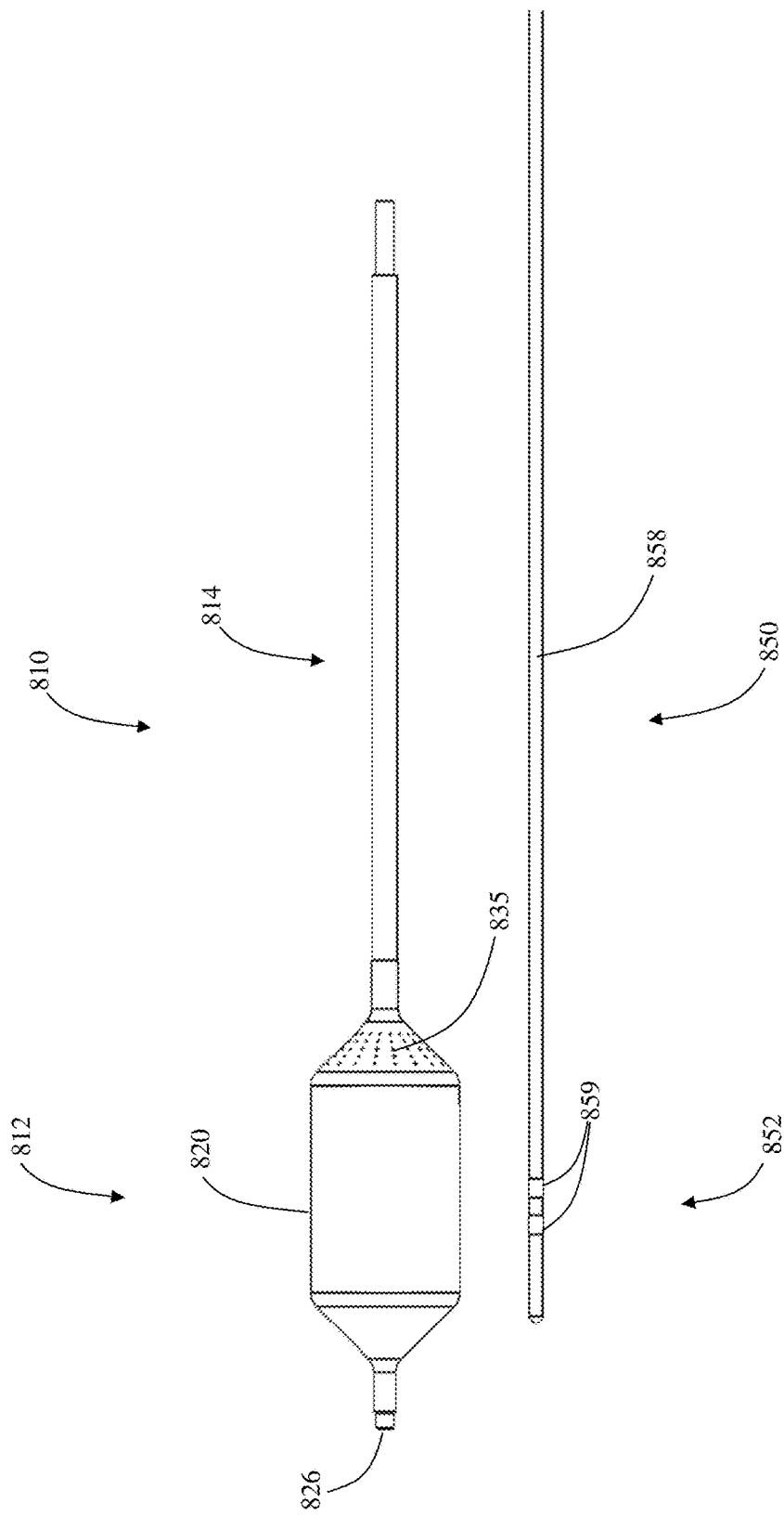
FIGS. 21-23 depict a dual catheter embodiment of a cooled microwave denervation catheter similar to that depicted in FIG. 8.
Figure 22:
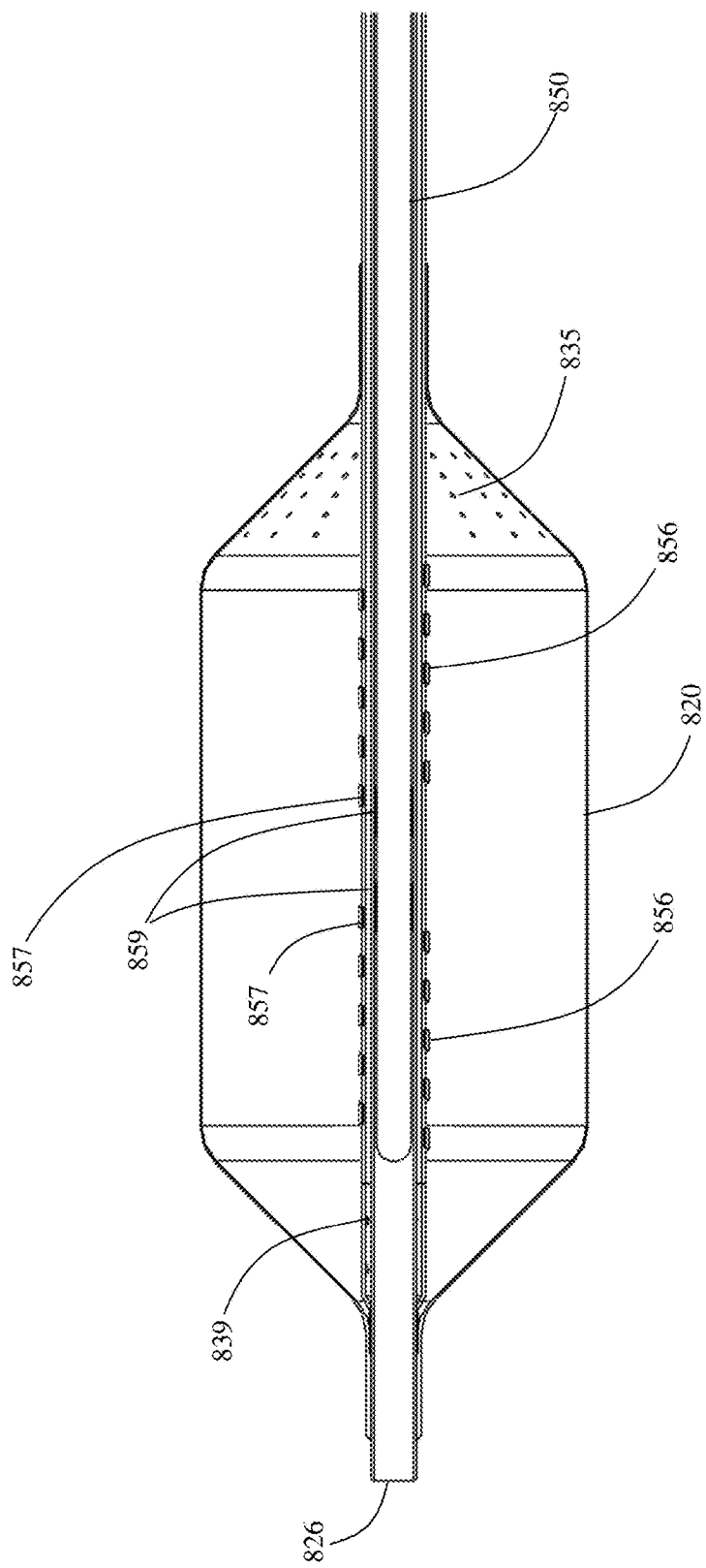
Figure 23:
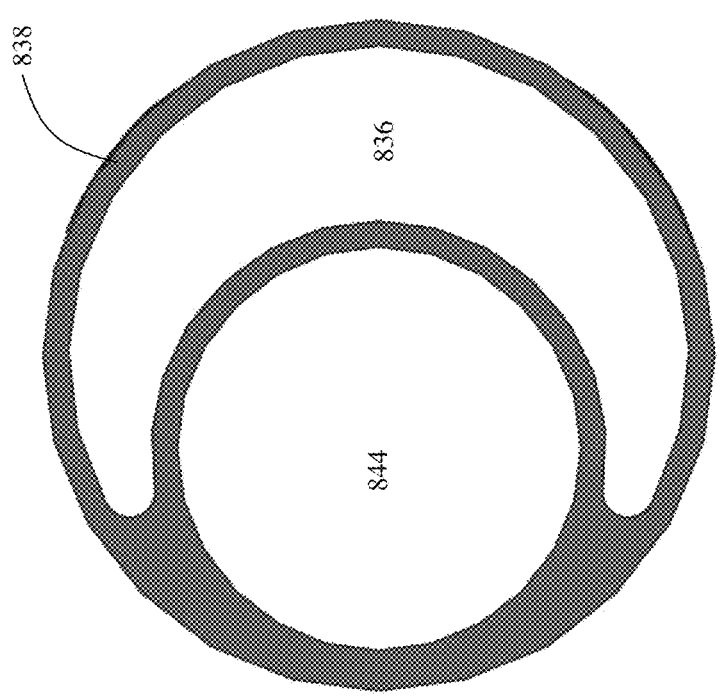

FIGS. 21, 22, and 23 depict a dual catheter embodiment similar to that depicted in FIG. 8. Cooling balloon/antenna catheter 810 includes central lumen 844 through which either a guide catheter or a coaxial cable catheter exits orifice 826 at the tip. Coaxial cable catheter 850 is initially separate from cooling balloon catheter 810, so that catheter 810 may be placed over a guide wire and positioned within body lumen adjacent the desired denervation site. Once placed, the guide wire is removed and coaxial cable catheter 850 is advanced within lumen 844 in catheter 810 so that contacts 859 on coaxial cable catheter engage with mating contacts, 857 within catheter 810. Coolant flows through a relatively large lumen 836 into balloon 820 through orifice 839 and into the interior of balloon 820. Coolant exits balloon 820 through apertures 835 on the proximal taper of the balloon and is discharged into body lumen as described above in previous embodiments.

Radio opaque markers 846 may be incorporated if helpful for placement.

As can be appreciated, apertures 835 on balloon 820 may be located on the proximal taper as shown in FIG. 22, on the distal taper like those shown in FIG. 19, or on both proximal and distal tapers as shown in FIG. 20. Alternately, the discharge holes may be located on the cylindrical wall of balloon 820. Coolant port 839 may be moved within balloon in order to ensure that coolant is moving along body lumen contact area so that cooling may be accomplished.

FIG. 24 depicts an alternate cross section for the shaft of catheter 810. In this figure, as in FIG. 23, the outer tubing wall is identified as 838. The cooling lumen is 836, and the antenna catheter/guide wire lumen is 844.

This concept combines the shared guidewire and coaxial cable lumen concept in DNX-001 with the cooling fluid holes in the balloon tapers as in DNX-008 B, C & D. The shaft of the treatment catheter requires only two lumens. One lumen is a shared lumen for guidewire and coaxial cable and the second lumen is for inflow of cooling fluid. The lumen configuration can be either a simple coaxial design or multilumen extrusion.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of performing denervation with a cooled microwave denervation catheter assembly that includes a catheter body having at least one fluid passage and an interior lumen therein, the interior lumen having a first portion in a first axial region, a second portion in a second axial region, and a taper between the first portion and the second portion, the second portion having a smaller diameter than the first portion, and also includes a balloon in communication with the at least one fluid passage to receive cooling fluid for inflating the balloon into a shape that surrounds the catheter body at the first portion of the interior lumen, the method comprising:

advancing the catheter body over a guide wire in a body lumen of a patient to a treatment location adjacent targeted nerves, the guide wire being located in the interior lumen of the catheter body;

inflating the balloon with the cooling fluid to contact a wall of the body lumen of the patient;

removing the guide wire from the interior lumen of the catheter body;

inserting a microwave antenna catheter into the interior lumen of the catheter body, the microwave antenna catheter including a coaxial cable and a microwave antenna connectable to a microwave generator to supply power to the microwave antenna to cause microwave energy to be emitted from the microwave antenna, a distal end of the microwave antenna catheter engaging the taper between the first portion and the second portion of the catheter body so as to position the microwave antenna in the first portion of the interior lumen; and performing denervation treatment by simultaneously circulating the cooling fluid in the balloon and supplying power to the microwave antenna to cause microwave energy to be emitted from the microwave antenna toward the targeted nerves, wherein the power supplied to the microwave antenna and the cooling fluid circulated in the balloon are controlled to cause the targeted nerves to be heated to a temperature sufficient to cause thermal damage while the wall of the body lumen of the patient is maintained at a temperature where thermal damage does not occur.

2. The method of claim 1, wherein the method further comprises, after performing the denervation treatment, discontinuing flow of cooling fluid in the balloon, deflating the balloon, and removing the catheter body and the microwave antenna catheter from the body lumen of the patient.

3. The method of claim 1, wherein the body lumen of the patient is a renal artery of the patient.

\* \* \* \* \*